US010744078B2

(12) United States Patent
Dake et al.

(10) Patent No.: US 10,744,078 B2
(45) Date of Patent: *Aug. 18, 2020

(54) COMPOSITIONS AND METHODS FOR TOPICAL APPLICATION AND TRANSDERMAL DELIVERY OF BOTULINUM TOXINS

(71) Applicant: Revance Therapeutics, Inc., Newark, CA (US)

(72) Inventors: Michael D Dake, Stanford, CA (US); Jacob M Waugh, Palo Alto, CA (US)

(73) Assignee: REVANCE THERAPEUTICS, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/140,288

(22) Filed: Sep. 24, 2018

(65) Prior Publication Data

US 2019/0247293 A1    Aug. 15, 2019

Related U.S. Application Data

(63) Continuation of application No. 14/935,886, filed on Nov. 9, 2015, now Pat. No. 10,080,786, which is a continuation of application No. 11/367,642, filed on Mar. 3, 2006, now Pat. No. 9,180,081.

(60) Provisional application No. 60/658,434, filed on Mar. 3, 2005.

(51) Int. Cl.
| *A61K 38/48* | (2006.01) |
| *A61K 9/00* | (2006.01) |
| *A61K 8/64* | (2006.01) |
| *A61Q 19/08* | (2006.01) |
| *A61K 47/34* | (2017.01) |

(52) U.S. Cl.
CPC .............. *A61K 8/64* (2013.01); *A61K 9/00* (2013.01); *A61K 9/0014* (2013.01); *A61K 38/4893* (2013.01); *A61K 47/34* (2013.01); *A61Q 19/08* (2013.01); *A61K 9/0019* (2013.01); *A61K 2800/56* (2013.01); *C12Y 304/24069* (2013.01)

(58) Field of Classification Search
None
See application file for complete search history.

(56) References Cited

U.S. PATENT DOCUMENTS

| 4,078,060 A | 3/1978 | Benson et al. |
| 4,434,228 A | 2/1984 | Swann |
| 4,816,568 A | 3/1989 | Hamilton, Jr. et al. |
| 5,252,713 A | 10/1993 | Morgan, Jr. et al. |
| 5,260,082 A | 11/1993 | Delvalle et al. |
| 5,420,105 A | 5/1995 | Gustavson et al. |
| 5,512,547 A | 4/1996 | Johnson et al. |
| 5,607,691 A | 3/1997 | Hale et al. |
| 5,629,020 A | 5/1997 | Leone-Bay et al. |
| 5,709,861 A | 1/1998 | Santiago et al. |
| 5,714,468 A | 2/1998 | Binder |
| 5,744,166 A | 4/1998 | Illum |
| 5,747,641 A | 5/1998 | Frankel et al. |
| 5,756,468 A | 5/1998 | Johnson et al. |
| 5,766,605 A | 6/1998 | Sanders et al. |
| 5,795,587 A | 8/1998 | Gao et al. |
| 5,804,604 A | 9/1998 | Frankel et al. |
| 5,877,278 A | 3/1999 | Zuckerman |
| 5,985,434 A | 11/1999 | Qin et al. |
| 5,989,545 A | 11/1999 | Foster |
| 6,217,912 B1 | 4/2001 | Park et al. |
| 6,228,161 B1 | 5/2001 | Drummond |
| 6,280,937 B1 | 8/2001 | Luo et al. |
| 6,306,423 B1 | 10/2001 | Donovan et al. |
| 6,312,708 B1 | 11/2001 | Donovan |
| 6,383,509 B1 | 5/2002 | Donovan et al. |
| 6,413,941 B1 | 7/2002 | Garnett et al. |
| 6,444,209 B1 | 9/2002 | Johnson |
| 6,447,787 B1 | 9/2002 | Gassner et al. |
| 6,458,763 B1 | 10/2002 | Peterson et al. |
| 6,495,663 B1 | 12/2002 | Rothbard et al. |
| 6,506,399 B2 | 1/2003 | Donovan |
| 6,511,676 B1 | 1/2003 | Boulikas |
| 6,544,548 B1 | 4/2003 | Siller-Jackson et al. |
| 6,585,993 B2 | 7/2003 | Donovan et al. |

(Continued)

FOREIGN PATENT DOCUMENTS

| EP | 1005867 | 6/2000 |
| EP | 1180524 | 2/2002 |

(Continued)

OTHER PUBLICATIONS

Sonntag et al, PsychoNeuro 2005, 31/6:315-320 . . . Abstract Only (Year: 2005).*

(Continued)

*Primary Examiner* — Nita M. Minnifield
(74) *Attorney, Agent, or Firm* — Ballard Spahr LLP

(57) ABSTRACT

Improved formulations for transdermal delivery of botulinum toxin are disclosed. The formulations include, for example, botulinum toxin non-covalently associated with a positively charged backbone having branching or efficiency groups. The formulations also include a partitioning agent, oligo-bridge, or polyanion bridge, and may optionally contain a viscosity modifying agent. The formulations are designed for topical application onto the skin of a patient and may be used to treat wrinkles, hyperhidrosis, and other health-related problems. Kits for administration are also described.

20 Claims, 22 Drawing Sheets

(15 of 22 Drawing Sheet(s) Filed in Color)

Specification includes a Sequence Listing.

(56) References Cited

U.S. PATENT DOCUMENTS

| | | |
|---|---|---|
| 6,593,292 B1 | 7/2003 | Rothbard et al. |
| 6,610,820 B1 | 8/2003 | Bonny |
| 6,627,632 B2 | 9/2003 | Parks et al. |
| 6,645,501 B2 | 11/2003 | Dowdy |
| 6,669,951 B2 | 12/2003 | Rothbard et al. |
| 6,670,322 B2 | 12/2003 | Goodnough et al. |
| 6,680,301 B2 | 1/2004 | Berg et al. |
| 6,683,049 B1 | 1/2004 | Aoki et al. |
| 6,688,311 B2 | 2/2004 | Hanin |
| 6,692,746 B1 | 2/2004 | Terman et al. |
| 6,692,911 B2 | 2/2004 | Pack et al. |
| 6,696,038 B1 | 2/2004 | Mahato et al. |
| 6,730,293 B1 | 5/2004 | Rothbard et al. |
| 6,759,387 B2 | 7/2004 | Rothbard et al. |
| 6,773,928 B1 | 8/2004 | Yin et al. |
| 6,831,059 B2 | 12/2004 | Donovan |
| 6,844,324 B1 | 1/2005 | Zhang et al. |
| 6,855,688 B2 | 2/2005 | McKerracher |
| 6,866,856 B2 | 3/2005 | Lu et al. |
| 6,896,886 B2 | 5/2005 | Aoki et al. |
| 6,958,147 B1 | 10/2005 | Alitalo et al. |
| 6,974,578 B1 | 12/2005 | Aoki et al. |
| 7,008,924 B1 | 3/2006 | Yan et al. |
| 7,056,656 B1 | 6/2006 | Rana et al. |
| 7,060,498 B1 | 6/2006 | Wang |
| 7,138,105 B2 | 11/2006 | Bolotin |
| 7,255,865 B2 | 8/2007 | Walker |
| 7,807,780 B2 | 10/2010 | Waugh et al. |
| 7,729,525 B2 | 11/2010 | Frevert |
| 7,829,525 B2 | 11/2010 | Frevert |
| 7,883,720 B2 | 2/2011 | Lynn et al. |
| 8,022,179 B2* | 9/2011 | Dake .................. A61K 8/64 530/326 |
| 8,092,788 B2* | 1/2012 | Dake ............... A61K 49/0041 424/78.02 |
| 8,137,677 B2 | 3/2012 | Hunt |
| 8,168,206 B1 | 5/2012 | Hunt |
| 8,218,414 B2 | 7/2012 | Takahashi |
| 8,398,997 B2* | 3/2013 | Dake .................. A61K 8/64 424/247.1 |
| 8,404,249 B2* | 3/2013 | Dake .................. A61K 8/64 424/247.1 |
| 8,518,414 B2* | 8/2013 | Waugh .............. A61K 8/64 424/239.1 |
| 8,568,740 B2* | 10/2013 | Waugh .............. A61K 8/64 424/236.1 |
| 8,586,020 B2 | 11/2013 | Song et al. |
| 8,642,047 B2 | 2/2014 | Hunt |
| 8,680,069 B2 | 3/2014 | de Fougerolles et al. |
| 8,974,774 B2* | 3/2015 | Dake ............... A61K 49/0041 424/78.02 |
| 9,180,081 B2* | 11/2015 | Dake .................. A61K 8/64 |
| 9,211,248 B2* | 12/2015 | Dake .................. A61K 9/0014 |
| 9,314,416 B2* | 4/2016 | Dake .................. A61K 8/64 |
| 9,340,587 B2 | 5/2016 | Thompson |
| 9,737,500 B2 | 8/2017 | Bannister |
| 9,795,577 B2 | 10/2017 | Bannister |
| 9,956,435 B2* | 5/2018 | Ruegg ............... A61K 8/64 |
| 10,080,786 B2* | 9/2018 | Dake .................. A61K 8/64 |
| 10,105,421 B2* | 10/2018 | Taylor ............... A61K 8/64 |
| 10,111,939 B2* | 10/2018 | Thompson .......... A61K 39/08 |
| 10,172,877 B2* | 1/2019 | Dake ............... A61K 49/0041 |
| 10,201,594 B2* | 2/2019 | Ruegg ............. A61K 38/4893 |
| 10,322,085 B2* | 6/2019 | Tamarkin ........... A61K 8/362 |
| 10,406,290 B2* | 9/2019 | Vogt ................... A61P 25/14 |
| 10,532,019 B2* | 1/2020 | Edelson ............. A61K 8/062 |
| 10,549,042 B2* | 2/2020 | Vogt ................... A61K 9/0019 |
| 10,576,034 B2* | 3/2020 | Edelson ........... A61K 38/4893 |
| 2001/0024716 A1 | 9/2001 | Chen et al. |
| 2002/0006905 A1 | 1/2002 | Aoki et al. |
| 2002/0009491 A1 | 1/2002 | Rothbard et al. |
| 2002/0086036 A1 | 7/2002 | Walker |
| 2002/0107199 A1 | 8/2002 | Walker |
| 2002/0127247 A1 | 9/2002 | Steward et al. |
| 2002/0131965 A1 | 9/2002 | Rothbard et al. |
| 2003/0022831 A1 | 1/2003 | Rothbard et al. |
| 2003/0027752 A1 | 2/2003 | Steward et al. |
| 2003/0032593 A1 | 2/2003 | Wender et al. |
| 2003/0083256 A1 | 5/2003 | Rothbard et al. |
| 2003/0104622 A1 | 6/2003 | Robbins et al. |
| 2003/0109448 A1 | 6/2003 | Crowley et al. |
| 2003/0113349 A1* | 6/2003 | Coleman, III ....... A61K 9/0014 424/239.1 |
| 2003/0118598 A1 | 6/2003 | Hunt |
| 2003/0130722 A1 | 7/2003 | Marx et al. |
| 2003/0138437 A1 | 7/2003 | Hunt |
| 2003/0147921 A1 | 8/2003 | Goodnough et al. |
| 2003/0147958 A1 | 8/2003 | Ahn et al. |
| 2003/0157134 A1 | 8/2003 | Aoki et al. |
| 2003/0162719 A1 | 8/2003 | Rothbard et al. |
| 2003/0165567 A1 | 9/2003 | Mixson |
| 2003/0185788 A1 | 10/2003 | Rothbard et al. |
| 2003/0215395 A1 | 11/2003 | Yu et al. |
| 2003/0215412 A1 | 11/2003 | Waugh |
| 2003/0219462 A1 | 11/2003 | Steward et al. |
| 2003/0220480 A1 | 11/2003 | Bonny |
| 2003/0229034 A1 | 12/2003 | Waugh et al. |
| 2003/0236214 A1 | 12/2003 | Wolff et al. |
| 2004/0009180 A1 | 1/2004 | Donovan |
| 2004/0009469 A1 | 1/2004 | Apt et al. |
| 2004/0013687 A1 | 1/2004 | Simpson |
| 2004/0013692 A1 | 1/2004 | Aoki et al. |
| 2004/0033241 A1 | 2/2004 | Donovan |
| 2004/0037853 A1 | 2/2004 | Borodic |
| 2004/0109871 A1 | 6/2004 | Pascual |
| 2004/0127556 A1 | 7/2004 | Lu et al. |
| 2004/0147443 A1 | 7/2004 | Renault |
| 2004/0161405 A9 | 8/2004 | Rothbard et al. |
| 2004/0186045 A1 | 9/2004 | Rothbard et al. |
| 2004/0192754 A1 | 9/2004 | Shapira et al. |
| 2004/0220100 A1 | 11/2004 | Waugh et al. |
| 2004/0220386 A1 | 11/2004 | Steward et al. |
| 2004/0242518 A1 | 12/2004 | Chen et al. |
| 2004/0247614 A1 | 12/2004 | Dorr et al. |
| 2004/0247623 A1 | 12/2004 | Cady |
| 2004/0265935 A1 | 12/2004 | Atassi |
| 2005/0074461 A1 | 4/2005 | Donovan |
| 2005/0074466 A1 | 4/2005 | Suskind et al. |
| 2005/0112146 A1 | 5/2005 | Graham |
| 2005/0175636 A1 | 8/2005 | Donovan |
| 2005/0196414 A1 | 9/2005 | Dake et al. |
| 2005/0232966 A1 | 10/2005 | Hughes et al. |
| 2005/0238667 A1 | 10/2005 | Hunt |
| 2005/0239705 A1 | 10/2005 | Dake et al. |
| 2006/0018931 A1 | 1/2006 | Taylor |
| 2006/0024331 A1 | 2/2006 | Fernandez-Salas |
| 2006/0040882 A1 | 2/2006 | Chen |
| 2006/0122096 A1 | 6/2006 | Rozema et al. |
| 2007/0077259 A1 | 4/2007 | Dake et al. |
| 2007/0148189 A1 | 6/2007 | Moyer et al. |
| 2008/0038203 A1 | 2/2008 | Dake et al. |
| 2008/0064863 A1 | 3/2008 | Nagasaki et al. |
| 2008/0200373 A1 | 8/2008 | Waugh et al. |
| 2008/0226551 A1 | 9/2008 | Waugh et al. |
| 2008/0233152 A1 | 9/2008 | Waugh et al. |
| 2009/0087457 A1 | 4/2009 | Dake et al. |
| 2010/0021502 A1 | 1/2010 | Waugh et al. |
| 2010/0028385 A1 | 2/2010 | Nassif |
| 2010/0062484 A1 | 3/2010 | Aebi et al. |
| 2010/0093639 A1 | 4/2010 | Waugh et al. |
| 2010/0116664 A1 | 5/2010 | Ignatius et al. |
| 2010/0166689 A1 | 7/2010 | Waugh |
| 2010/0168023 A1 | 7/2010 | Ruegg et al. |
| 2010/0330123 A1 | 12/2010 | Thompson et al. |
| 2011/0020229 A1 | 1/2011 | Waugh et al. |
| 2011/0097357 A1 | 4/2011 | Fernandez et al. |
| 2011/0206731 A1 | 8/2011 | First |
| 2011/0268765 A1 | 11/2011 | Ruegg et al. |
| 2012/0014894 A1 | 1/2012 | Waugh |
| 2012/0065131 A1* | 3/2012 | Dake .................. A61K 8/64 514/12.1 |
| 2012/0107361 A1 | 5/2012 | Thompson et al. |
| 2012/0148562 A1 | 6/2012 | Ho et al. |

(56) References Cited

U.S. PATENT DOCUMENTS

| | | | |
|---|---|---|---|
| 2012/0282241 A1 | 11/2012 | Rimando | |
| 2013/0033252 A1 | 2/2013 | Ignatius | |
| 2013/0071444 A1 | 3/2013 | Wang et al. | |
| 2013/0197397 A1 | 8/2013 | Waugh | |
| 2013/0202636 A1 | 8/2013 | Dake | |
| 2013/0251770 A1 | 9/2013 | Waugh | |
| 2014/0072981 A1 | 3/2014 | Clemons et al. | |
| 2014/0120077 A1 | 5/2014 | Ruegg et al. | |
| 2014/0154237 A1 | 6/2014 | Waugh | |
| 2015/0320781 A1 | 11/2015 | Dake | |
| 2016/0051646 A1 | 2/2016 | Dake | |
| 2016/0114014 A1* | 4/2016 | Dake | A61K 9/0014 424/94.3 |
| 2016/0250302 A1 | 9/2016 | Ruegg | |
| 2017/0157020 A1* | 6/2017 | Waugh | A61Q 19/08 |
| 2017/0348262 A1 | 12/2017 | Bannister | |
| 2017/0361130 A9* | 12/2017 | Modi | A61K 38/4893 |
| 2018/0214717 A1* | 8/2018 | Ruegg | A61K 8/64 |
| 2018/0311333 A1* | 11/2018 | Ruegg | A61K 8/64 |
| 2019/0008795 A1* | 1/2019 | Waugh | A61K 9/7023 |
| 2019/0055310 A1* | 2/2019 | Arnason | C07K 14/765 |
| 2019/0105261 A1* | 4/2019 | Waugh | A61K 9/0014 |
| 2019/0247293 A1* | 8/2019 | Dake | A61K 8/64 |
| 2019/0336691 A1* | 11/2019 | Vogt | C12Y 304/24069 |
| 2020/0054722 A1* | 2/2020 | Edelson | A61B 5/4266 |
| 2020/0054869 A1* | 2/2020 | Liu | A61K 9/0021 |
| 2020/0093791 A1* | 3/2020 | Bodor | A61K 47/12 |

FOREIGN PATENT DOCUMENTS

| | | |
|---|---|---|
| EP | 1185291 | 3/2002 |
| EP | 1421948 | 5/2004 |
| EP | 1477183 | 11/2004 |
| EP | 0737074 | 10/2006 |
| EP | 2656859 | 10/2013 |
| JP | 63-287730 | 11/1988 |
| JP | 11-60475 | 3/1999 |
| JP | 2001-511171 | 2/2002 |
| JP | 2002-524527 | 8/2002 |
| RU | 2203058 | 4/2003 |
| RU | 2207844 | 7/2003 |
| WO | WO 1992/07871 | 5/1992 |
| WO | WO 1994/04686 | 3/1994 |
| WO | WO 1995017904 | 7/1995 |
| WO | WO 1996011712 | 4/1996 |
| WO | WO 199740854 | 11/1997 |
| WO | WO 1998019710 | 5/1998 |
| WO | WO 1998022610 | 5/1998 |
| WO | WO 1998034648 | 8/1998 |
| WO | WO 1999024596 | 5/1999 |
| WO | WO 1999042901 | 8/1999 |
| WO | WO 1999043350 | 9/1999 |
| WO | WO 200024419 | 5/2000 |
| WO | WO 200034308 | 6/2000 |
| WO | WO 2000032764 | 6/2000 |
| WO | WO 2001013957 | 3/2001 |
| WO | WO 2001062297 | 8/2001 |
| WO | WO 200207773 | 1/2002 |
| WO | WO 2002065986 | 8/2002 |
| WO | WO 2002067917 | 9/2002 |
| WO | WO 2002069930 | 9/2002 |
| WO | WO 2003049772 | 6/2003 |
| WO | WO 2003072049 | 9/2003 |
| WO | WO 2003097107 | 11/2003 |
| WO | WO 2004006954 | 1/2004 |
| WO | WO 2005/002597 | 1/2005 |
| WO | WO 2005007185 | 1/2005 |
| WO | WO 2005/084361 | 9/2005 |
| WO | WO 2005/084410 | 9/2005 |
| WO | WO 2006005910 | 1/2006 |
| WO | WO 2006/094193 | 9/2006 |
| WO | WO 2006/094263 | 9/2006 |
| WO | WO 2007/059528 | 5/2007 |
| WO | WO 2013/112974 | 8/2013 |
| WO | WO 2014/066916 | 5/2014 |
| WO | WO-2019075263 A2 * | 4/2019 ............... A61K 8/64 |

OTHER PUBLICATIONS

Odderson et al, Arch Phys Med REhabil., 1998, 79:350-352 (Year: 1998).*

Moreau et al, British J Dermatology, 2003, 149:1041-1045 (Year: 2003).*

McConaghy et al. AM Fam Physician. Jun. 1, 2018, 97/11:729-734. (Year: 2008).*

Mayo Clinic, 1998, Hyperhidrosis, 3 pages (Year: 1998).*

Lim et al, Medical Hpotheses. 2006, 67:27-32. (Year: 2006).*

Crissman, Craniofacial Hyperhidrosis: Causes and Treatment Options | My Carpe. Jul. 14, 2018, 7 pages (Year: 2018).*

Crissman, Botox for Axillary Hyperhidrosis | My Carpe. Aug. 17, 2018, 7 pages (Year: 2018).*

Heckman et al New England Journal of Medicine, Feb. 15, 2001, 344/7:488-493. (Year: 2001).*

Connolly et al, Am J Clin Dermatol, 2003, 4/10:681-697 (Year: 2003).*

Baumann et ak, International Journal of Dermatology, 2005, 44:418-424 (Year: 2005).*

Lowe et al, Dermatol. Surg. May 2003., 29/5:545-548 (Year: 2003).*

Author: E O'Toole A A, O'Toole E Article or Chapter Title: Botulinum toxin for idiopathic and acromegaly-associated palmar and axillary hyperhidrosis Journal or Book Title: Br.J.Dermatol. / Br.J.Dermatol. 2000, 143 Suppl. 57, 43 (abstract only) (Year: 2000).*

"AIDS, Use of HIV-1 TAT, to target and/or activate antigen-presenting cells, and/or to deliver cargo molecules" from http://pharmalicensing.com/public/outlicensing/view/3766 (2001).

Ambache, N. "A further survey of the action of clostridium botulinum toxin upon different types of autonomic nerve fibre". J. Physiol. (1951), 113, 1-17.

Bergmann I., et al. "Selective degeneration of sudomotor fibers in Ross Syndrome and successful treatment of compensatory hyperhidrosis with botulinum toxin", Muscle & Nerve 21(12):1790-1793, 1998.

Blanes-Mira et al., "Identification of Snare complex Modulators that Inhibit Exocytosis from an Alpha-Helix-Constrained Combinatorial Library," Biochem. J., vol. 375(1), pp. 159-166, Oct. 1, 2003.

Blanes-Mira et al., "Small peptides after the N-Terminus domain of Snap25 Inhibit Snare complex assembly and regulated exocytosis," J. of Neurochem., vol. 88(1), pp. 124-135, Jan. 2004.

Blanes-Mira et al., "A Synthetic Hexapeptide Argireline with Antiwrinkle Activity," Int'l J. of Cosmetic Science, vol. 24(5), pp. 303-310, 2002.

Bowie et al., "Deciphering the Message in Protein Sequences: Tolerance to Amino Acid Substitutions," Science, 247, pp. 1306-1310, 1990.

Brooks et al., "TAT Peptide-Mediated Cellular Delivery: Back to Basics," Advanced Drug Delivery Reviews, 57, pp. 559-577, 2005.

Calnan et al., "Analysis of Arginine-Rich Peptides from the HIV TAT Protein Reveals Unusual Features of RNA-Protein Recognition," Genes and Development, 5, pp. 201-210, 1991.

Cappel et al., "Effect of Nonionic Surfactants on Transderaml Drug Delivery: II. Poloxamer and Poloxamine Surfacts," International Journal of Pharmaceutics, 69, pp. 155-167, 1991.

Chen et al., "Biophysical Characterization of the Stablity of the 150-Kilodalton Botulinum Toxin, the Nontoxic Component, and the 900-Kilodalton Botulinum Toxin Complex Species," Infection and Immunity, Jun. 1998, vol. 66,No. 6,pp. 2420-2425.

Chen et al., "Long-time Molecular Dynamics Simulations of Botulinum Biotoxin Type A at Different pH Values and Temperatures," Journal of Molecular Model, vol. 13, pp. 559-572, 2007.

Communication Pursuant to Article 94(3) EPC issued for European Patent Application No. 05724470.9, dated Oct. 19, 2010, 7 pages.
Communication Pursuant to Article 94(3) EPC issued for European Patent Application No. 05759520.9, dated Oct. 1, 2010, 7 pages.

(56) References Cited

OTHER PUBLICATIONS

Console et al., "Antennapedia and HIV Transactivator of Transcription (TAT) Promote Endocytosis of High Molecular Weight Cargo Upon Binding to Cell Surface Clycosaminoglycans", J. Biol. Chem. vol. 278, No. 37, pp. 35109-35114, 2003.
Thomas E. Creighton, in his book, "Proteins: Structures and Molecular Properties," 1984, pp. 314-315.
Thomas E. Creighton, in his book, "Protein Structure: A Practical Approach," 1989, pp. 184-186.
Cristiano et al., "Hepatic Gene Therapy: Efficient Gene Delivery and Expression in Primary Hepatocytes Utilizing a Conjugated Adenovirus-DNA complex," Proc. Nat. Acad. Sci., 90: 11548-11552, 1993.
Crosland et al., "Detection of Sparse Botulinum Toxin A Binding Sites using Fluorescent Latex Microspheres", J. of Histotechnology, vol. 22, No. 2, pp. 113-115, Jun. 1999.
Fawell et al., "TAT-mediated Delivery of Heterologous Proteins into Cells," Proc. Natl. Acad. Sci., vol. 91, pp. 664-668, Jan. 1994.
Fisher et al., "Matrix Sialoprotein of Developing Bone," J. Biol. Chem., vol. 258, pp. 12723-12727, Oct. 1983.
Fletcher et al., Partially Modified Retro-Inverso Peptides: Development, Synthesis, and Conformational Behavior, Chem. Rev., 98(2): 763-795, 1998.
Futaki et al., "Internalization of Branched Arginine Peptides into Cells," 27[P1]I-120, The Pharmaceutical Society of Japan, Abstract, 123(2), Mar. 2003.
Futaki, "Intracellular Delivery of Biopolymers Using Membrane-Permeable Peptides," Membrane, 28(2), pp. 55-60, 2003.
Futaki et al., "Novel Method for Introducing Protein into Cells Using Arginine Peptides," 27[P1]I-118, Institute for Chemical Research, 123(2), p. 26, Mar. 2003.
GenBank Accession No. M77788 (2005).
George et al., "Electrically Controlled Drug Delivery from Biotin-Doped Conductive Polypyrrole," Adv. Mater., 18, pp. 577-581, 2006.
Glogau, R., "Botulinum toxin A neurotoxin for axillary hyperhidrosis—no sweat Botox", Dermatol surg. Aug. 1998 24(8) 817-819.
Green, M. "Mutational analysis of HIV-1 TAT minimal domain peptides: identification of trans-dominant mutants that suppress HIV-LTR-driven gene expression", Cell, 58:215-223, 1989.
Heckman, M. Et al. "Botulinum toxin for axillary hyperhidrosis (excessive sweating)", N. Engl. J. Med. 344(7) 488-493, 2001.
Huber et al., "Efficient In Vitro Transfection of Human Keratinocytes with an Adenovirus-Enhanced Receptor-Mediated System," The Journal of Investigative Dermatology, pp. 661-666, 2000.
Kabonov et al., "Interpolyelectrolyte and Block Ionomer Complexes for Gene Delivery: Physico-Chemical Aspect," Advanced Drug Delivery Reviews, 30, 49-60, 1998.
Kabouridis, "Biological Application of Protein Transduction Technology," Trends in Biotechnology, vol. 21, No. 11, pp. 498-503, Nov. 2003.
Kalderon et al., "A Short Amino Acid Sequence Able to Specify Nuclear Location," Cell, vol. 39, pp. 499-509, 1984.
Kim, et al. "Sequence Requirements for the Assembly of Simian Virus 40 T Antigen and the T-Antigen Origin Binding Domain on the Viral Core Origin of Replication", J. Virol., Sep. 1999, pp. 7543-7555.
Knight et al., "Non-Viral Neuronal Gene Delivery Mediated by the HC Fragment of Tetanus Toxin," Eur. J. Biochem., 259, 762-769, 1999.
Lieber et al., "Adenoviral Preterminal Protein Stabilizes Mini-Adenoviral Genomes in Vitro and in Vivo," Nature Biotechnology, vol. 15, pp. 1383-1387, Dec. 15, 1997.
Lim, E. et al. "Topical botulinum toxin to treat hyperhidrosis? No sweat!" Medical Hypotheses, vol. 67, Issue 1, pp. 27-32, 2006.
Martinez-Fong et al., "Neurotensin-SPDP-poly-L-lysine conjugate: a NonViral Vecto for Targeted Gene Delivery to Neural Cells," Molecular Brain Research, 59(2), 249-262, 1999.

Morris et al., "A Peptide Carrier for the Delivery of Biologically Active Proteins into Mammalian Cells," Nature Biotechnology, vol. 19, Dec. 1, 2001, pp. 1173-1176.
Murdan, "A Review of Pluronic Lecithin Organogel as a Topical and Transdermal Drug Delivery System," Hospital Pharmacist, vol. 12, pp. 267-270, 2005.
Naujoks et al., "Using Local Surface Charges for the Fabrication of Protein Patterns," Colloids and Surfaces A: Physicochem. Eng. Aspects, 249, pp. 69-72, 2004.
Naumann, M. et al. "Focal Hyperhidrosis—Effective Treatment with Intracutaneous Botulinum Toxin", Arch Dermatol. 134, 301-304, 1998.
Naver H., "The treatment of focal hyperhidrosis with botulinum toxin", Eur J Neurol 1997; 4(Suppl 2):S75-9.
Nosoh et al., "Protein Stability and Stabilization through Protein Engineering," 1991, chapter 7, pp. 197-217.
Odderson, I., "Axillary hyperhidrosis: Treatment with Botulinum Toxin A", Arch Phys Med Rehabil 79(3):350-2, 1998.
Park et al., "Mutational Analysis of a Human Immunodeficiency Virus Type 1 Tat Protein Transduction Domain Which is Required for Delivery of an Exogenus Protein into Mammalian Cells," Journal of General Virology, 2002, 83, pp. 1173-1181.
Paul et al., "Transdermal Immunisation with an Integral Membrane Component, Gap Junction Protein, By Means of Ultradeformable Drug Carriers, Transfersomes," Vaccine, 1998, 16(2/3), pp. 188-195.
Pierce Protein Research Projects, "EZ-Link Sulfo-NHS-Biotin and Biotinylation Kits," http://www.piercenet.com/objects/view.cfm?type=productfamily&ID=01030904, retrieved on May 19, 2004.
Pirrung, "Molecular Diversity and Combinatorial Chemistry: Principles and Application," Elsevier, Netherlands, First Edition (2004), p. 137.
Printout of website on Jul. 20, 2005 for "botulinum cream" from http://www.ebigchina.com/ebcps/4/pd/82305.html.
Puls et al, "Gene Transfer and Expression of a Non-Viral Polycation-Based Vector in CD4+ Cells," Gene Therapy, 6: 1774-1778, 1999.
Schantz et al., "Properties and Use of Botulinum Toxin and Other Microbial Neurotoxins in Medicine". Microbiological Reviews, col. 56, No. 1, Mar. 1992, pp. 80-89.
Schwartz et al., "Peptide-Mediated Cellular Delivery" Curr. Opin. Mol. Ther. vol. 2, No. 2 pp. 162-167, 2000.
Shalaby, "Polymers for Augmenting Botulinum Vaccine Efficiency"—Abstract, 1998.
Somerman et al., Human Bone Sialoprotein I and II Enhance Fibroblast Attachment in Vitro, Calcif. Tissue Intl., 43, pp. 50-53, 1988.
Sun et al. entitled "Mutations in the intersubunit bridge regions of 16S rRNA affect decoding and subunit-subunit interactions on the 70S ribosome," Nucleic Acids Research, 2011, vol. 39(8), p. 3321-3330.
Terrorist Use of Toxins and Poisons Information for Laboratory Professionals, Assistant Secretary for Preparedness and Response (ASPR), Department of Health and Human Services, USA, Nov. 2010, 2 pages.
Definition of Poloxamer from the free Encyclopedia from Wikipedia, Sep. 10, 2008.
Thompson et al., "The Complete Amino Acid Sequence of the Clostridium Botulinum type A Neurotoxin, Deduced by Nucleotide Sequence Analysis of the Encoding Gene," Eur. J. Biochem., 189, pp. 73-81, 1990, GenBank Accession X52066.1, 1993.
Toncheva et al., "Novel Vectors for Gene Delivery Formed by Self-Assembly of DNA with poly(L-lysinc) Grafted with Hydrophilic Polymers," Biochimica et Biophysica Acta., 1380(3), 354-368, 1998.
Uike et al., "Efficiency of Targeted Gene Delivery of Ligand-Poly-L-Lysine Hybrids with Different CrossLinks," Bioscience, Biotechnology, and Biochemistry, 62(6), 1247-1248, 1998.
Umezawa et al., "Development of β-peptides Having Ability to Penetrate Cell Membrane," 27[P1]I-133, Faculty of Pharmaceutical Sciences, Nagoya City University, 123(2), p. 29, Mar. 2003.

(56) References Cited

OTHER PUBLICATIONS

Vives et al., "A Truncated HIV-1 TAT Protein Basic Domain Rapidly Translocates Through the Plasma Membrane and Accumulates in the Cell Nucleus," J. Biol. Chem., 275(25), pp. 16010-16017, Jun. 1997.
Wang et al., "Histone H1-like Protein Participates in Endothelial Cell-Specific Activation of the von Willebrand Factor Promoter," Blood, 104(6): 1725-1732, 2004.
Wender et al., "The Design, Synthesis and Evaluation of Molecules that Enable or Enhance Cellular Uptake: Peptoid Molecular Transporters," PNAS, 97:24, 13003-13008, Nov. 21, 2000.
Ziegler et al., "Interaction of the Protein Transduction Domain of HIV-1 TAT with Heparan Sulfate: Binding Mechanism and Thermodynamic Parameters," Biophysical Journal, vol. 86, pp. 254-263, Jan. 2004.
Urbanova et al., "Noncovalent interaction of peptides with porphyrins in aqueous solution: conformational study using vibrational CD spectroscopy", Biopolymers (Peptide Science), col. 60, pp. 307-316, 2001.
Voet et al., Biochemistry, Second Edition, John Wiley and Sons, Inc., pp. 1275-1276, 1995.
Wu et al., "Receptor-Mediated in Vitro Gene Transformation by a Soluabl DNA Carrier System," J. Biol. Chem, 262(10): 4429-4432, 1987.
Yano et al., "Control of Hair Growth and Follicle Size by VEGF-Mediated Angiogensis," J. Clin. Invest., 107:409-417, 2001.
1992 Sigma Catalog, p. 1745.
Mammalian Expression, 1998 Promega Catalog, pp. 262-265.
http:www.genlantis.com/catalog/product_line.cfm?product_family_key=13&product_line_key=54, retrieved from the internet on Sep. 2, 2005.
Alexandra Sifferlin, Botox:The Drug That's Treating Everything, Time, Jan. 5, 2017. 12 pages vol. 189, No. 3 (Year: 2017).
Garcia-Murray et al, Dermatol Surg, January Supplement 2015;41:S47-S55.
Ruegg et al, Abstracts Toxins 2011 / Toxicon 68 (2013)119-120, (abstract only) http://dx.doi.org/10.1016/j.toxicon.2012.07.161.
Press Release, Revance Therapeutics, Inc., "Revance Reports Results for RT001 Topical Phase 3 Trial for Lateral Canthal Lines", Jun. 13, 2016.

\* cited by examiner

Revance's botulinum formulation

FIGURE 3A

Baseline

FIGURE 3B

Revance's botulinum formulation

Baseline

FIGURE 4

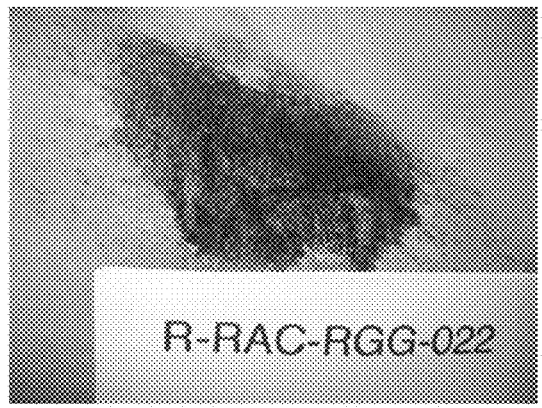 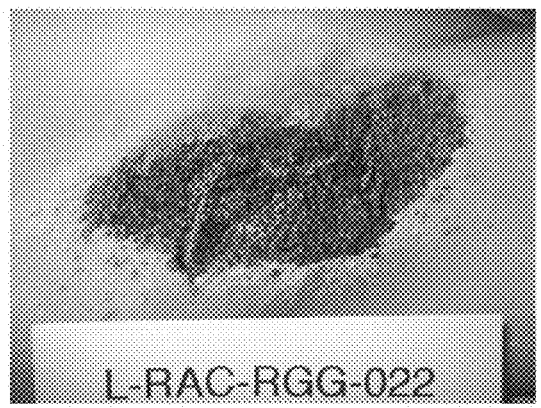
FIGURE 9A　　　　　　　　　　　　FIGURE 9B
 
FIGURE 9C　　　　　　　　　　　　FIGURE 9D

Porcine Skin Flux - Topical Toxin

Skin Flux Delivery (%) vs Topical Toxin - Carrier:Toxin Mass Ratio, Toxin amount

- K30TS 0:1, 0.05 ug - loofah
- K30TS 1:1, 0.05 ug - loofah
- K30TS 0:1, 0.05 ug
- K30TS 1:1, 0.05 ug

FIGURE 14B

Porcine Skin Flux - Topical Toxin

Skin Flux Delivery (%) vs Topical Toxin - Carrier:Toxin Mass Ratio, Toxin amount

- Control 0:1
- K30TS 1:1
- K15T2 1:1
- K15T2 1.1:1
- K30TS 1.1:1

FIGURE 14C

Porcine Skin Flux - Topical Toxin

Topical Toxin - Carrier:Toxin Mass Ratio, Toxin amount

FIGURE 14D

Porcine Skin Flux - Topical Toxin

Topical Toxin - Carrier:Toxin Mass Ratio, Toxin amount

FIGURE 14E

Porcine Skin Flux - Topical Toxin

Topical Toxin - Carrier:Toxin Mass Ratio, Toxin amount

FIGURE 14F

Porcine Skin Flux - Topical Toxin

Topical Toxin - Carrier:Toxin Mass Ratio, Toxin amount

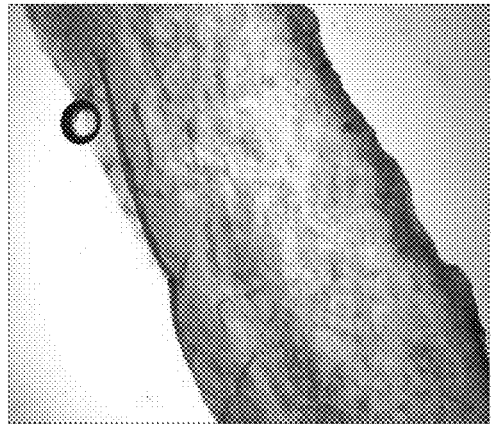
FIGURE 15A  FIGURE 15B
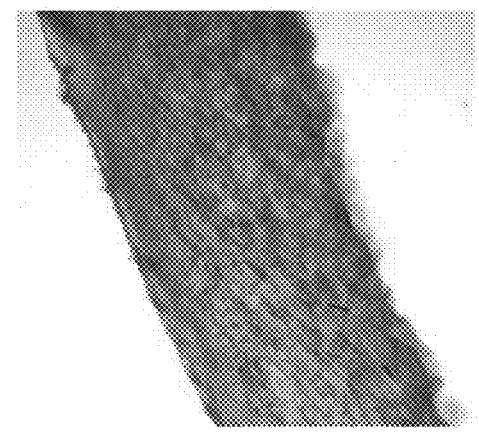
FIGURE 15C  FIGURE 15D
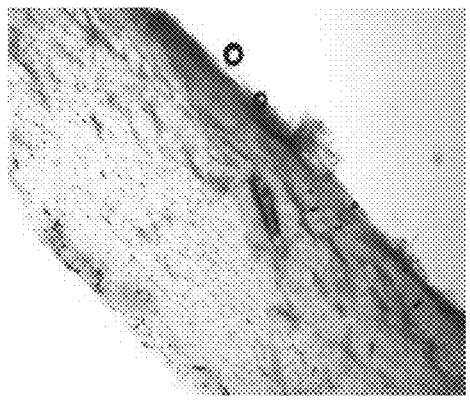
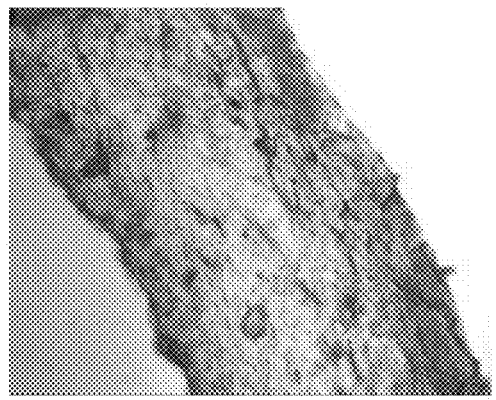
FIGURE 15E  FIGURE 15F FIGURE 17A   FIGURE 17B   FIGURE 17C
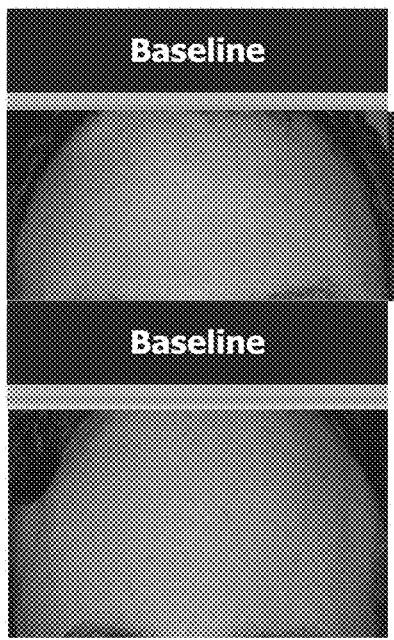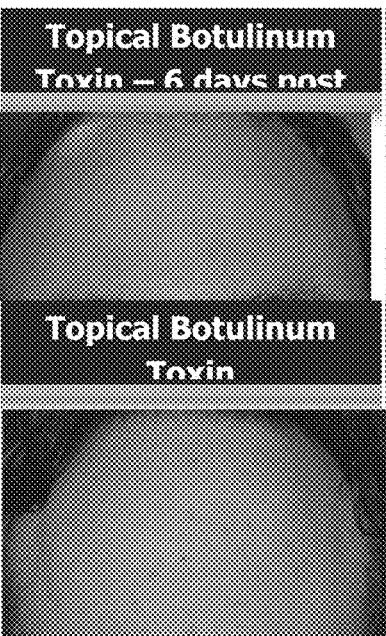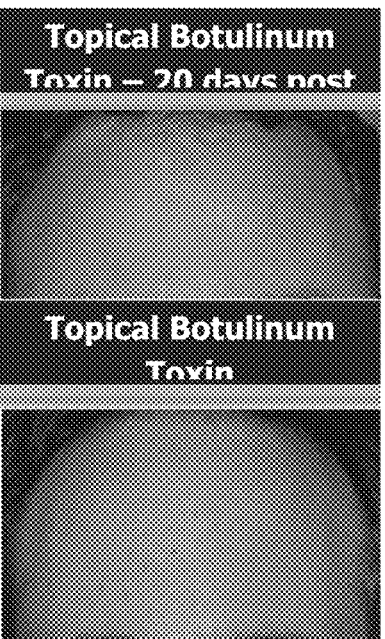
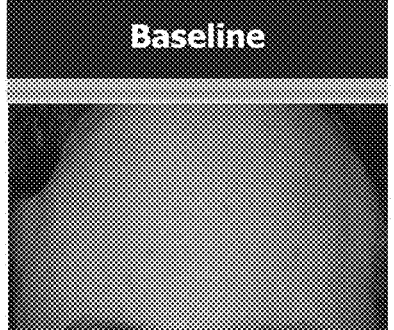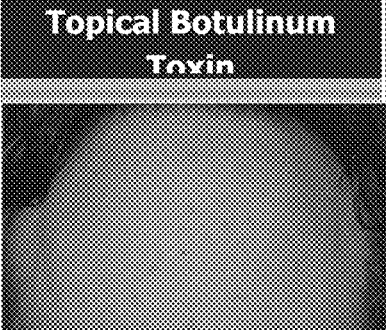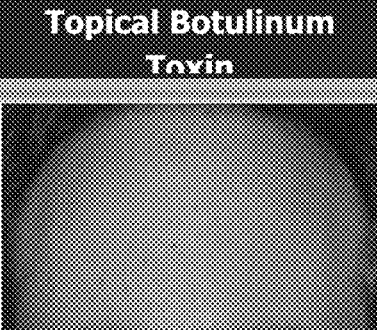
FIGURE 17D   FIGURE 17E   FIGURE 17F

SEQUENCE LISTING

```
<160> NUMBER OF SEQ ID NOS: 5

<210> SEQ ID NO 1
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 Gly residues
<220> FEATURE:
```

```
<221> NAME/KEY: MOD_RES
<222> LOCATION: (26)..(45)
<223> OTHER INFORMATION: This region may encompass 5-25 Arg residues
<220> FEATURE:
<223> OTHER INFORMATION: see specification as filed for detailed
      description of substitutions and preferred embodiments

<400> SEQUENCE: 1

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg
            20                  25                  30

Arg Arg Arg Arg Arg Arg Arg Arg Arg Arg Arg Arg Arg
            35                  40                  45

<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 Gly residues
<220> FEATURE:
<221> NAME/KEY: MOD_RES
<222> LOCATION: (32)..(51)
<223> OTHER INFORMATION: This region may encompass 0-20 Gly residues
<220> FEATURE:
<223> OTHER INFORMATION: see specification as filed for detailed
      description of substitutions and preferred embodiments

<400> SEQUENCE: 2

Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
            35                  40                  45

Gly Gly Gly
    50

<210> SEQ ID NO 3
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 Gly residues
<220> FEATURE:
<221> NAME/KEY: MOD_RES
<222> LOCATION: (32)..(51)
<223> OTHER INFORMATION: This region may encompass 0-20 Gly residues
<220> FEATURE:
<223> OTHER INFORMATION: see specification as filed for detailed
      description of substitutions and preferred embodiments

<400> SEQUENCE: 3

Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30
```

```
Gly Gly Gly Gly Gly Gly Gly Gly Gly Gly Gly Gly Gly Gly Gly
         35                  40                  45

Gly Gly Gly
     50

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 Gly residues
<220> FEATURE:
<221> NAME/KEY: MOD_RES
<222> LOCATION: (30)..(49)
<223> OTHER INFORMATION: This region may encompass 0-20 Gly residues
<220> FEATURE:
<223> OTHER INFORMATION: see specification as filed for detailed
      description of substitutions and preferred embodiments

<400> SEQUENCE: 4

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly Gly
            20                  25                  30

Gly Gly Gly Gly Gly Gly Gly Gly Gly Gly Gly Gly Gly Gly Gly
         35                  40                  45

Gly

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Arg Arg Arg Arg Arg Arg Arg
1               5                   10
```

COMPOSITIONS AND METHODS FOR TOPICAL APPLICATION AND TRANSDERMAL DELIVERY OF BOTULINUM TOXINS

This application is a continuation of patent application U.S. Ser. No. 15/935,886, filed on Nov. 9, 2015, now U.S. Pat. No. 10,080,786, which is a continuation of patent application U.S. Ser. No. 11/367,642, filed on Mar. 3, 2006, now U.S. Pat. No. 9,180,081, which claims benefit of U.S. Provisional Patent Application No. 60/658,434, filed on Mar. 3, 2005, the contents of all of which are hereby incorporated by reference in their entireties.

BACKGROUND OF THE INVENTION

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: *People's Medical Society*, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. In addition, the dermis is also home to most of the skin's structures, including sweat and oil glands (which secrete substances through openings in the skin called pores, or comedos), hair follicles, nerve endings, and blood and lymph vessels (Inlander, Skin, New York, N.Y.: *People's Medical Society*, 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: *People's Medical Society*, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

One of the principal functions of skin is to provide a barrier to the transportation of water and substances potentially harmful to normal homeostasis. The body would rapidly dehydrate without a tough, semi-permeable skin. The skin helps to prevent the entry of harmful substances into the body.

Wrinkles, one of the telltale signs of aging, can be caused by biochemical, histological, and physiologic changes that accumulate from environmental damage (Benedetto, *International Journal of Dermatology*, 38:641-655 (1999)). In addition, there are other secondary factors that can cause characteristic folds, furrows, and creases of facial wrinkles (Stegman et al., The Skin of the Aging Face, *Cosmetic Dermatological Surgery*, $2^{nd}$ ed., St. Louis, Mo.: Mosby Year Book: 5-15 (1990)). These secondary factors include the constant pull of gravity, frequent and constant positional pressure on the skin (i.e., during sleep), and repeated facial movements caused by the contraction of facial muscles (Stegman et al., The Skin of the Aging Face, *Cosmetic Dermatological Surgery*, $2^{nd}$ ed., St. Louis, Mo.: Mosby Year Book: 5-15 (1990)).

Different techniques have been utilized in order potentially to mollify some of the signs of aging. These techniques range from facial moisturizers containing alpha hydroxy acids and retinol to surgical procedures and injections of neurotoxins. For example, in 1986, Jean and Alastair Carruthers, a husband and wife team consisting of an ocuplastic surgeon and a dermatologist, began to evolve the cosmetic use of the type A form of botulinum toxin for treatment of movement-associated wrinkles in the *glabella* area (Schantz and Scott, In Lewis G E (Ed) *Biomedical Aspects of Botulinum*, New York: Academic Press, 143-150 (1981)). The Carruthers' use of botulinum type A for the treatment of wrinkles led to their seminal publication of this approach in 1992 (Schantz and Scott, In Lewis G E (Ed) *Biomedical Aspects of Botulinum*, New York: Academic Press, 143-150 (1981)). By 1994, the same team reported experiences with other movement-associated wrinkles on the face (Scott, *Ophthalmol*, 87:1044-1049 (1980)). This in turn led to the birth of the era of cosmetic botulinum type A treatment.

In addition to botulinum type A, there are seven other botulinum toxins that are serologically related, but distinct. Generally, botulinum toxins (also known as botulin toxins or botulinum neurotoxins) are neurotoxins produced by the gram-positive bacteria *Clostridium botulinum*. They act to produce paralysis of muscles by preventing synaptic transmission or release of acetylcholine across the neuromuscular junction, and are thought to act in other ways as well. Their action essentially blocks signals that normally would cause muscle spasms or contractions, resulting in paralysis.

Of the eight serologically related botulinum toxins, seven can cause paralysis, namely botulinum neurotoxin serotypes A, B, C, D, E, F and G. Each of these is distinguished by neutralization with type-specific antibodies. Nonetheless, the molecular weight of the botulinum toxin protein molecule, for all seven of these active botulinum toxin serotypes, is about 150 kD. As released by the bacterium, the botulinum toxins are complexes comprising the 150 kD botulinum toxin protein molecule in question along with associated non-toxin proteins. The botulinum toxin type A complex can be produced by Clostridia bacterium as 900 kD, 500 kD and 300 kD forms. Botulinum toxin types B and C are apparently produced as only a 700 kD or 500 kD complex. Botulinum toxin type D is produced as both 300 kD and 500 kD complexes. Botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg, about 12 times the primate $LD_{50}$ for type A. Due to the molecule size and molecular structure of botulinum toxin, it cannot cross stratum corneum and the multiple layers of the underlying skin architecture.

The toxic condition resulting from systemic botulinum toxin exposure (referred to as botulism) has existed in Europe since antiquity. In 1895, Emile P. van Ermengem first isolated the anaerobic spore-forming *bacillus* from raw salted pork meat obtained from post-mortem tissue of victims who died of botulism in Belgium. Van Ermengem found the disease to be caused by an extracellular toxin that was produced by what he called *Bacillus botulinus* (Van Ermengem, Z Hyyg Infektionskr, 26:1-56; *Rev Infect* (1897)). The name was changed in 1922 to *Clostridium botulinum*. The name *Clostridium* was used to reflect the anaerobic nature of the microorganism and also its morphologic characteristics (Carruthers and Carruthers, *Can J Ophthalmol*, 31:389-400 (1996)). In the 1920's, a crude form of Botulinum toxin type A was isolated after additional outbreaks of food poisoning. Dr. Herman Sommer at the University of California, San Francisco made the first attempts to purify the neurotoxin (Borodic et al., *Ophthalmic Plast Recostr Surg*, 7:54-60 (1991)). In 1946, Dr. Edward J. Schantz and his colleagues isolated the neurotoxin in crystalline form (Schantz et al., In: Jankovi J, Hallet M (Eds), *Therapy with Botulinum Toxin*, New York, N.Y.: Marcel Dekker, 41-49 (1994)). By 1949, Burgen and his associates were able to demonstrate that the botulinum toxin blocks impulses across the neuromuscular junction (Burgen et al., *J Physiol*, 109:10-24 (1949)). Allan B. Scott first used botulinum toxin A (BTX-A) in monkeys in 1973. Scott demonstrated reversible ocular muscle paralysis lasting 3 months (Lamanna, *Science*, 130:763-772 (1959)). Soon afterwards, BTX-A was reported to be a successful treatment in humans for strabismus, blepharospasm, and spasmodic torticollis (Baron et al., In: Baron E J, Peterson L R, Finegold S M (Eds), Bailey & Scotts *Diagnostic Microbiology*, St. Louis, Mo.: Mosby Year Book, 504-523 (1994); Carruthers and Carruthers, *Adv Dermatol*, 12:325-348 (1997); Markowitz, In: Strickland G T (Eds) *Hunters Tropical Medicine*, 7$^{th}$ ed. Philadelphia: W.B. Saunders, 441-444 (1991)). Botulinum toxin type A is said to be the most lethal natural biological agent known to man. Spores of *C. botulinum* are found in soil and can grow in improperly sterilized and sealed food containers. Ingestion of the bacteria can cause botulism, which can be fatal.

At the same time, the muscle-paralyzing effects of botulinum toxin have been used for therapeutic effects. Controlled administration of botulinum toxin has been used to provide muscle paralysis to treat conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temperomandibular joint disorder, and various types of muscle cramping and spasms. More recently the muscle-paralyzing effects of botulinum toxin have been taken advantage of in therapeutic and cosmetic facial applications such as treatment of wrinkles, frown lines, and other results of spasms or contractions of facial muscles.

In view of both the toxicity of botulinum toxin, as well as its potential for therapeutic benefits, it would be desirable to develop compositions and methods for safe application of the toxin. Topical application of botulinum toxin would provide for a safer and more desirable treatment alternative due to the painless nature of application, the larger treatment surface area that can be covered, the ability to formulate a pure toxin with higher specific activity, the reduced training necessary for applying the botulinum therapeutic, the smaller doses that would be necessary to produce the desired effect, and the lack of a requirement for large wells of toxin to reach a therapeutic clinical result. An effective means for transdermal delivery of botulinum toxin, as well as an effective means for administering botulinum toxin to treat or prevent a number of conditions that does not require injection is thus highly desirable.

SUMMARY OF THE INVENTION

This invention relates to new compositions comprising a botulinum toxin, more specifically to such compositions that enable the transport or delivery of a botulinum toxin through the skin or epithelium (also referred to as "transdermal delivery"), and that therefore may be used as topical applications for providing a botulinum toxin to a subject, for various therapeutic, aesthetic and/or cosmetic purposes, as described herein.

One aspect of this invention is to provide a composition containing a botulinum toxin and a carrier. The carrier has a polymeric backbone with attached positively charged branching groups. The association between the carrier and the botulinum toxin is non-covalent.

This invention also provides a method of administering a botulinum toxin to a subject involving topically applying to the skin or epithelium of the subject the botulinum toxin in conjunction with an effective amount of a carrier. The carrier has a polymeric backbone with attached positively charged branching groups, and associates non-covalently with the botulinum toxin.

Another aspect of this invention is to provide formulations containing a botulinum toxin, a positively charged backbone, and at and at least one member selected from the group consisting of a partitioning agent, oligo-bridge, and polyanion bridge, such that the botulinum toxin is non-covalently complexed with the positively charged backbone. This formulation can be used to treat wrinkles by applying the formulation to an area of skin. If desired, an occlusion agent may be applied after application of the formulation.

The formulations of this invention can also be used to treat hyperhidrosis. Treatment methods contemplated by the invention include applying to an area of skin of the formulations of this invention and optionally applying an occlusion agent afterwards.

Another aspect of this invention is to provide a kit for administration of a botulinum toxin to a subject. The kit includes a botulinum toxin present in an effective amount for transdermal delivery thereof, and a carrier that has a polymeric backbone with attached positively charged branching groups. The association between the carrier and the botulinum toxin is non-covalent.

Yet another aspect of this invention is to provide a kit for administration of a botulinum toxin to a subject. The kit includes a device for delivering the botulinum toxin to the skin and a composition containing a carrier having a polymeric backbone with attached positively charged branching groups selected from -(gly)$_{n1}$-(arg)$_{n2}$ (SEQ ID NO:1), HIV-TAT and fragments thereof, and Antennapedia PTD, in which the subscript n1 is an integer of from 0 to about 20, and the subscript n2 is independently an odd integer of from about 5 to about 25.

In one aspect, this invention relates to a composition comprising a botulinum toxin (as defined herein) and a carrier comprising a positively charged "backbone" having positively charged branching or "efficiency" groups, as described herein. Most preferably the positively charged carrier is a long-chain positively charged polypeptide or a positively charged nonpeptidyl polymer, for example, a polyalkyleneimine. The invention further relates to a method for producing a biologic effect such as muscle paralysis, reducing hypersecretion or sweating, treating neurologic pain or migraine headache, reducing muscle spasms, preventing or reducing acne, or reducing or enhancing an immune response, by topically applying an effective amount of such a composition, preferably to the skin, of a subject or patient in need of such treatment. The invention also relates to a method for producing an aesthetic or cosmetic effect, for example by topical application of botulinum toxin to the face instead of by injection into facial muscles.

This invention also provides kits for preparing or formulating a composition that comprises the carrier and the botulinum toxin, as well as such additional items that are needed to produce a usable formulation, or a premix that may in turn be used to produce such a formulation. Alternatively the kit comprises means for separately but in conjunction administering the botulinum toxin and the carrier to a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B show photographs depicting wrinkles on subject's forehead before (FIG. 3A) and after (FIG. 3B) treatment with Revance's botulinum formulation topically.

Figure 4:
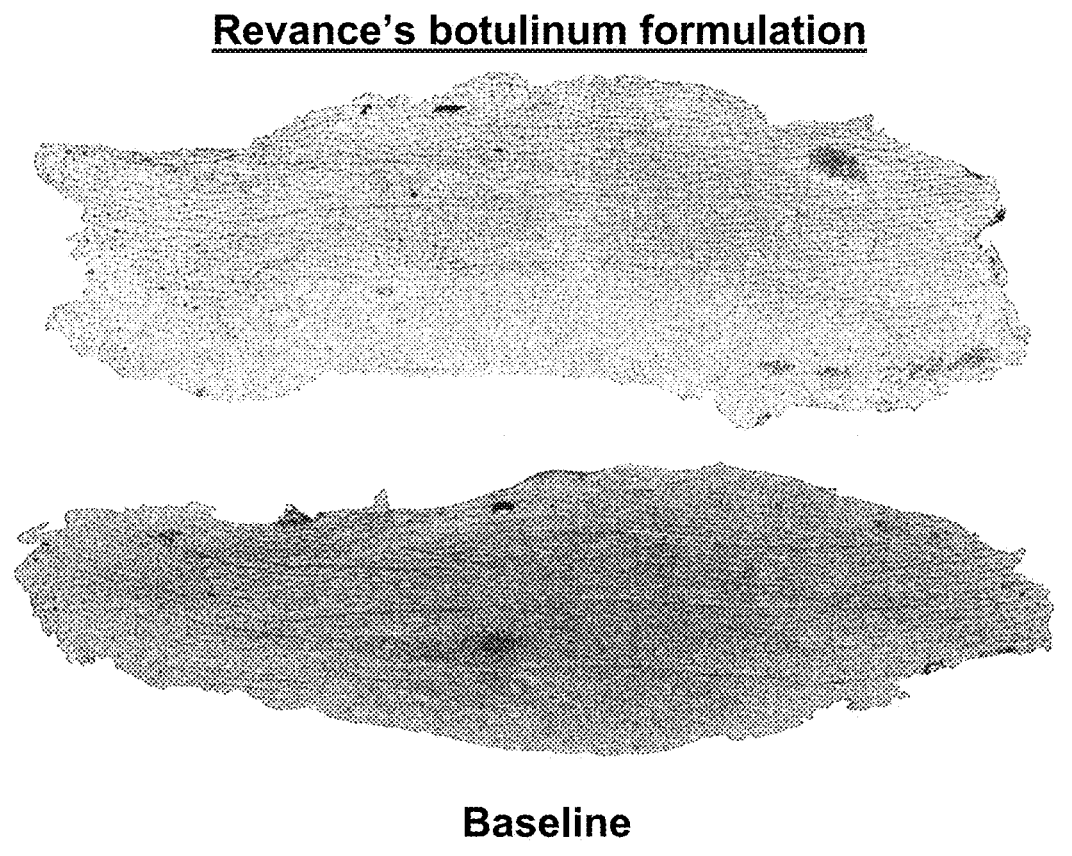

FIG. 4 shows a Mikrosil cast of the forehead (A) after topical treatment of wrinkles with Revance's botulinum formulation and (b) before treatment. These Mikrosil casts, which are useful because they minimize artifacts that can result from photographing the actual subject, clearly show that the untreated side has deeper wrinkles.

FIG. 6A shows a photograph depicting Minor's starch/iodine test two minutes after application of Revance's botulinum formulation and FIG. 6B shows a photograph depicting Minor's starch/iodine test two minutes after application of a control formulation. The control formulation contained a positively charged polylysine backbone with a molecular weight of about 21,000 and with TAT branching groups. These photographs were taken two minutes after application. FIG. 6C and FIG. 6D are the same as FIG. 6A and FIG. 6B, respectively, except that the photographs were taken after four minutes had elapsed.

FIG. 8A represents the results of an experiment demonstrating efficiency of botulinum toxin therapeutically delivered across intact skin as a topical agent using a short peptidyl carrier for the treatment of axillary hyperhidrosis on human subjects. Graph depicts significant reduction in amount of sweat (mg per 5 minutes) measured gravimetrically 4 weeks after treatment with BOTOX® plus a short peptidyl carrier or carrier alone. Results are 4 week values as ratio to baseline value for same group, with significance determined by Wilcoxon analysis with P<0.05. N=10 patients. FIG. 8B represents the results of an experiment demonstrating efficiency of botulinum toxin therapeutically delivered across intact skin as a topical agent using a short peptidyl carrier for the treatment of axillary hyperhidrosis on human subjects. Graph depicts significant reduction in amount of sweat (mg per 5 minutes) measured gravimetrically 4 weeks after treatment with BOTOX® plus a short peptidyl carrier or carrier alone. Results are treatment values as ratio to control value for both timepoints, with significance determined by Wilcoxon analysis with P<0.05. N=10 patients.

FIGS. 9A, 9B, 9C and 9D show photographs depicting Minor's starch/iodine test before and after treatment Revance's botulinum formulation topically for the treatment of axillary hyperhidrosis. Starch/iodine test at Baseline vs. 2 week is shown where right axilla was treated with Revance's botulinum formulation (Figures A and C) and left axilla was applied with the control (Figures B and D) for subject #12. These photographs illustrate typical benefits observed after treatment with carrier+botox in starch iodine. Although some crossover is observed on the control side (consistent with 25% reduction in gravimetric data), significant reductions are afforded with treatment (consistent with 65% reduction in gravimetric data on treated side).

FIG. 10A shows muscle force generation following application of a control formulation to a male CD1 mouse. FIG. 10B shows muscle force generation following application of topical "Revance BOTOX® solution" as described in Example 9.

FIG. 12A depicts apparatus setup, including reservoir, circulating water bath, inline peristaltic pump, inline Franz chambers, and fraction collector. FIG. 12B depicts cross-section of an individual Franz chamber, showing input and output tubing, skin membrane, and donor compound placement.

Figures 13A, 13B:
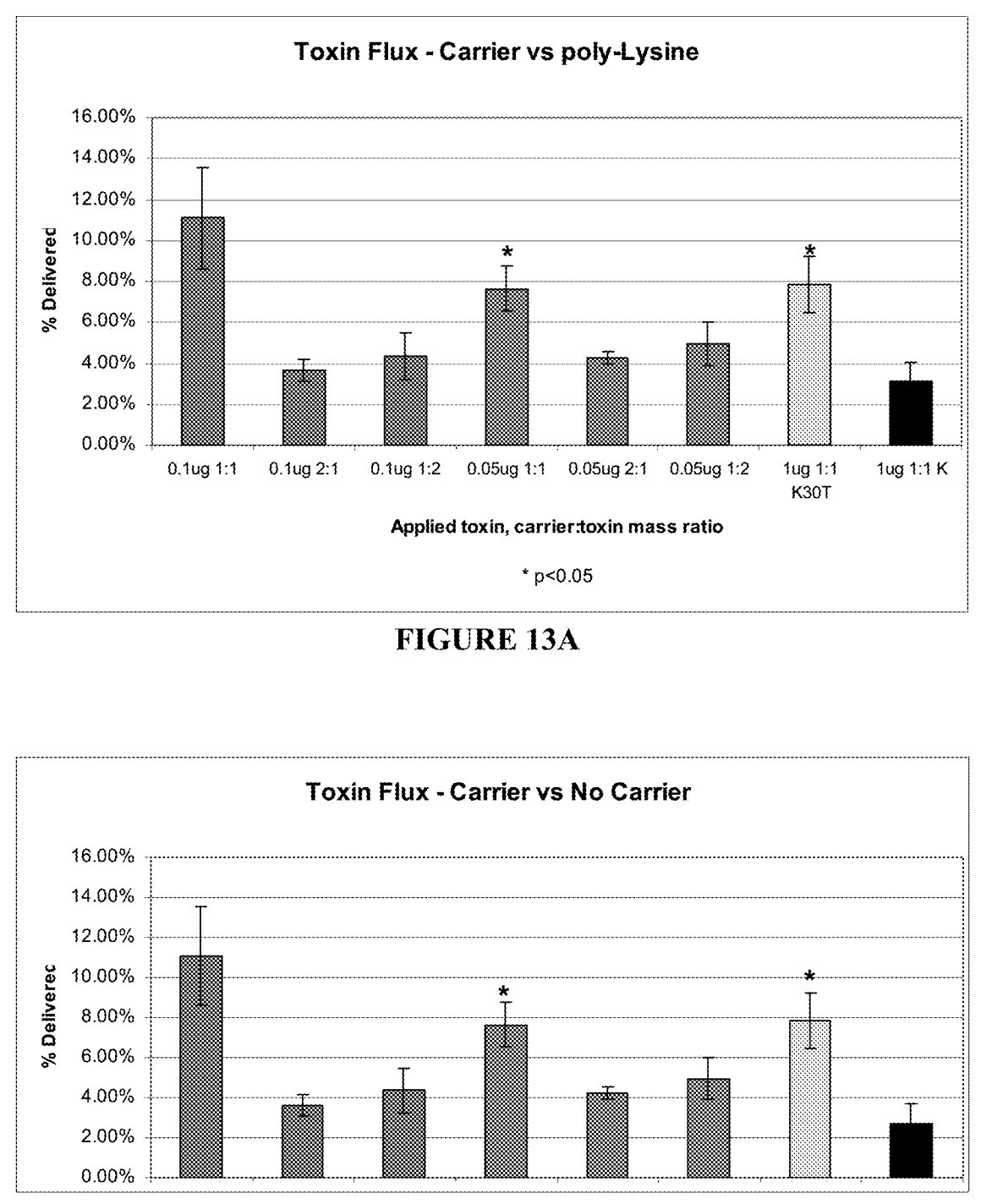

FIGS. 13A and 13B: Increased flux using K30T vs. controls. FIG. 13A depicts flux using K30T vs. poly-lysine; FIG. 13B depicts flux using K30T vs. no carrier.

FIGS. 14A, 14B, 14C, 14D, 14E and 14F: The efficiency of Revance carrier in delivering Botulinum Toxin Type A across the skin barrier in a porcine skin model was evaluated using modified Franz chamber. Increased flux of toxin after topical application is shown (FIGS. 14A-14F). Each figure depicts the mean and standard error percentage of topical toxin delivery across porcine skin with varying carrier:toxin mass ratios.

FIGS. 15A, 15B, 15C, 15D, 15E and 15F: Representative photomicrographs depicting streptavidin staining (blue positive) after topical application of: biotinylated botulinum toxin without carrier (control group, Figures A-C); or biotinylated botulinum toxin with K30 Ts carrier (treatment group, Figures D-F).

FIGS. 17A, 17B, 17C, 17D, 17E and 17F: Photographs showing reduce forehead wrinkles after topical botulinum toxin type A. Human subject 1 is in the top row and subject 2 is in the bottom row. The photographs illustrate pre-treatment (baseline) (FIGS. 17A and 17D) and post-treatment (FIGS. 17B-17C and 17E-17F).

DETAILED DESCRIPTION OF THE INVENTION

Figure 1:
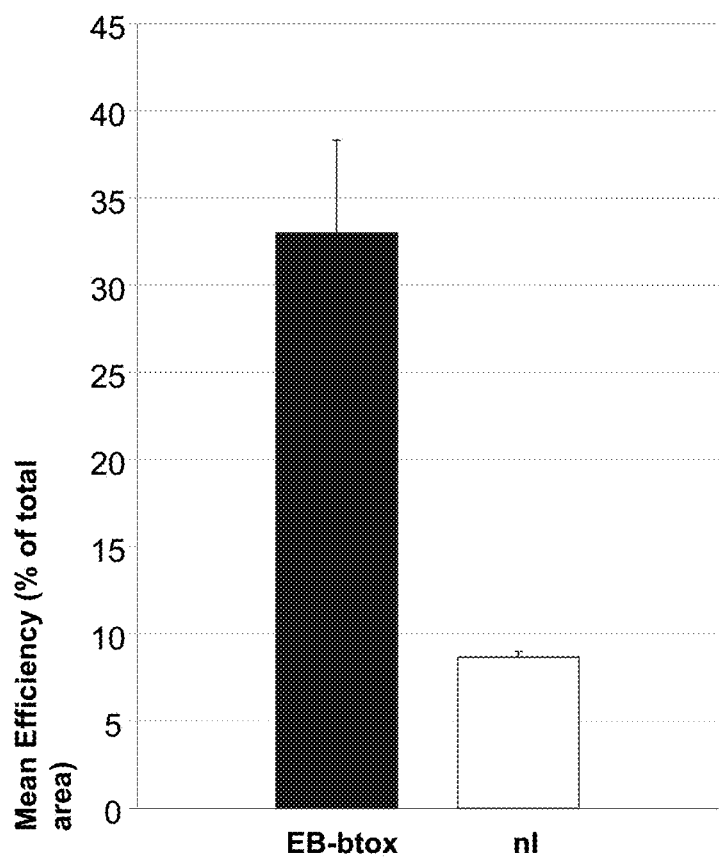
FIG. 1 represents the results of an experiment demonstrating efficiency of transdermal delivery of botulinum toxin using a composition of the invention comprising a peptide backbone.

This invention provides compositions and methods for delivery, particularly transdermal delivery, of a botulinum toxin by topical application of an appropriate formulation.

According to the present invention, a positively charged carrier molecule having efficiency groups, as described herein, has been found suitable as a transport system for a botulinum toxin, enabling that toxin to be administered transdermally to muscles and/or other skin-associated structures. The transport occurs without covalent modification of the botulinum toxin.

By "positively charged" is meant that the carrier has a positive charge under at least some solution-phase conditions, more preferably under at least some physiologically compatible conditions More specifically, "positively charged" as used herein, means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier (also referred to as a "positively charged backbone") is typically a linear chain of atoms, either with groups in the chain carrying a positive charge at physiological pH, or with groups carrying a positive charge attached to side chains extending from the backbone. Preferably, the positively charged backbone itself will not have a defined enzymatic or therapeutic biologic activity. The linear backbone is a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. In all aspects of the present invention, the association between the carrier and the biologically active agent is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight of from about 10,000 to about 1,500,000, more preferably from about 25,000 to about 1,200,000, most preferably from about 100,000 to about 1,000,000. One of skill in the art will appreciate that when amino acids are used in this portion of the invention, the sidechains can have either the D- or L-form (R or S configuration) at the center of attachment. Alternatively, the backbone can be an analog of a polypeptide such as a peptoid. See, for example, Kessler, *Angew. Chem. Int. Ed. Engl.* 32:543 (1993); Zuckermann et al. *Chemtracts-Macromol. Chem.* 4:80 (1992); and Simon et al. *Proc. Nat'l. Acad. Sci. USA* 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In one embodiment, the positively charged backbone is a polypeptide having branching groups (also referred to as efficiency groups). As used herein, an efficiency group or branching group is any agent that has the effect of promoting the translocation of the positively charged backbone through a tissue or cell membrane. Non-limiting examples of branching or efficiency groups include -(gly)$_{n1}$-(arg)$_{n2}$ (SEQ ID NO:1), HIV-TAT or fragments thereof, or the protein transduction domain of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. Still further preferred are those embodiments in which the HIV-TAT fragment has the formula (gly)$_p$-RGRDDRRQRRR-(gly)$_q$ (SEQ ID NO:2), (gly)$_p$-YGRKKRRQRRR-(gly)$_q$ (SEQ ID NO:3) or (gly)$_p$-RKKRRQRRR-(gly)$_q$ (SEQ ID NO:4) wherein the subscripts p and q are each independently an integer of from 0 to 20 and the fragment is attached to the backbone via either the C-terminus or the N-terminus of the fragment. Preferred HIV-TAT fragments are those in which the subscripts p and q are each independently integers of from 0 to 8, more preferably 2 to 5. In another preferred embodiment the positively charged side chain or branching group is the Antennapedia (Antp) protein transduction domain (PTD), or a fragment thereof that retains activity. Preferably the positively charged carrier includes side-chain positively charged branching groups in an amount of at least about 0.05%, as a percentage of the total carrier weight, preferably from about 0.05 to about 45 weight %, and most preferably from about 0.1 to about 30 weight %. For positively charged branching groups having the formula -(gly)$_{n1}$-(arg)$_{n2}$ (SEQ ID NO: 1), the most preferred amount is from about 0.1 to about 25%.

In another embodiment, the backbone portion is a polylysine and positively charged branching groups are attached to the lysine sidechain amino groups. The polylysine may have a molecular weight of from about 10,000 to about 1,500,000, preferably from about 25,000 to about 1,200,000, and most preferably from about 100,000 to about 1,000,000. It can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is preferably from one to four times the combined length of the negatively charged components. Preferred positively charged branching groups or efficiency groups include, for example, -gly-gly-gly-arg-arg-arg-arg-arg-arg-arg (-Gly$_3$Arg$_7$) (SEQ ID NO:5) or HIV-TAT. In another preferred embodiment the positively charged backbone is a long chain polyalkyleneimine such as a polyethyleneimine, for example, one having a molecular weight of about 1,000,000.

The positively charged backbones or carrier molecules comprising polypeptides or polyalkyleneimines, having the branching groups described above, are novel compounds and form an aspect of this invention.

In one embodiment of the invention, only a positively charged carrier that has positively charged branching groups is necessary for transdermal delivery of the botulinum toxin. In certain embodiments, the positively charged carrier is a polypeptide (e.g., lysine, arginine, omithine, homoarginine, and the like) having multiple positively charged side-chain groups, as described above. Preferably, the polypeptide has a molecular weight of at least about 10,000. In another embodiment, the positively charged carrier is a nonpeptidyl polymer such as a polyalkyleneimine having multiple positively charged side-chain groups having a molecular weight of at least about 100,000. Such polyalkyleneimines include polyethylene- and polypropyleneimines. In either instance, for use as the sole necessary agent for transdermal delivery the positively charged carrier molecule includes positively charged branching or efficiency groups, comprising -(gly)$_{n1}$-(arg)$_{n2}$ (SEQ ID NO:1), in which the subscript n1 is an integer of from 0 to 20 more preferably 0 to 8, still more preferably 2 to 5, and the subscript n2 is independently an odd integer of from about 5 to about 25, more preferably from about 7 to about 17, and most preferably from about 7 to about 13, HIV-TAT or fragments thereof, or Antennapedia PTD or a fragment thereof. Preferably the side-chain or branching groups have the general formula -(gly)$_{n1}$-(arg)$_{n2}$ (SEQ ID NO: 1) as described above. Other preferred embodiments are those in which the branching or efficiency groups are HIV-TAT fragments that have the formula (gly)$_p$-RGRDDRRQRRR-(gly)$_q$ (SEQ ID NO:2), (gly)$_p$-YGRKKRRQRRR-(gly)$_q$ (SEQ ID NO:3), or (gly)$_p$-RKKRRQRRR-(gly)$_q$ (SEQ ID NO:4), wherein the subscripts p and q are each independently an integer of from 0 to 20 and the fragment is attached to the carrier molecule via either the C-terminus or the N-terminus of the fragment. The side branching groups can have either the D- or L-form (R or S configuration) at the center of attachment. Preferred HIV-TAT fragments are those in which the subscripts p and q are each independently integers of from 0 to 8, more preferably 2 to 5. Other preferred embodiments are those in which the branching groups are Antennapedia PTD groups or fragments thereof that retain the group's activity. These are known in the art, for instance, from Console et al., J. Biol. Chem. 278:35109 (2003). Preferably, the positively charged carrier includes side-chain positively charged branching groups in an amount of at least about 0.05%, as a percentage of the total carrier weight, preferably from about 0.05 to about 45 weight %, and most preferably from about 0.1 to about 30 weight %. For positively charged branching groups having the formula -(gly)$_{n1}$-(arg)$_{n2}$ (SEQ ID NO: 1), the most preferred amount is from about 0.1 to about 25%.

In another embodiment, the carrier is a polylysine with positively charged branching groups attached to the lysine side-chain amino groups. The polylysine used in this particularly embodiment can be any of the commercially available (Sigma Chemical Company, St. Louis, Mo., USA, e.g.) polylysines such as, for example, polylysine having MW>70,000, polylysine having MW of 70,000 to 150,000, polylysine having MW 150,000 to 300,000 and polylysine having MW>300,000. However, preferably the polylysine has MW of at least about 10,000. Preferred positively charged branching groups or efficiency groups include, for example, -gly-gly-gly-arg-arg-arg-arg-arg-arg-arg (-Gly$_3$Arg$_7$) (SEQ ID NO:5), HIV-TAT or fragments of it, and Antennapedia PTD or fragments thereof.

In other embodiments of this invention, the carrier is a relatively short polylysine or polyethyleneimine (PEI) backbone (which may be linear or branched) and which has positively charged branching groups. Such carriers are useful for minimizing uncontrolled aggregation of the backbones and botulinum toxin in a therapeutic composition, which causes the transport efficiency to decrease dramatically. When the carrier is a relatively short linear polylysine or PEI backbone, the backbone will have a molecular weight of less than 75,000, more preferably less than 30,000, and most preferably, less than 25,000. When the carrier is a relatively short branched polylysine or PEI backbone, however, the backbone will have a molecular weight less than 60,000, more preferably less than 55,000, and most preferably less than 50,000. If, however, partitioning agents as described herein are included in the composition, the molecular weight of the branched polylysine and PEI backbones may be up to 75,000, while the molecular weight of the linear polylysine and PEI backbones may be up to 150,000.

The term "botulinum toxin" as used herein is meant to refer to any of the known types of botulinum toxin, whether produced by the bacterium or by recombinant techniques, as well as any such types that may be subsequently discovered including engineered variants or fusion proteins. As mentioned above, at the present time, seven immunologically distinct botulinum neurotoxins have been characterized, namely botulinum neurotoxin serotypes A, B, C, D, E, F and G, each of which is distinguished by neutralization with type-specific antibodies. The botulinum toxin serotypes are available from Sigma-Aldrich and from Metabiologics, Inc. (Madison, Wis.), as well as from other sources. The different serotypes of botulinum toxin vary in the animal species that they affect and in the severity and duration of the paralysis they evoke. At least two types of botulinum toxin, types A and B, are available commercially in formulations for treatment of certain conditions. Type A, for example, is contained in preparations of Allergan having the trademark BOTOX® and of Ipsen having the trademark DYSPORT®, and type B is contained in preparations of Elan having the trademark MYOBLOC®.

The botulinum toxin used in the compositions of this invention can alternatively be a botulinum toxin derivative, that is, a compound that has botulinum toxin activity but contains one or more chemical or functional alterations on any part or on any chain relative to naturally occurring or recombinant native botulinum toxins. For instance, the botulinum toxin may be a modified neurotoxin (e.g., a neurotoxin which has at least one of its amino acids deleted, modified or replaced, as compared to a native, or a recombinantly produced neurotoxin or a derivative or fragment thereof). For instance, the botulinum toxin may be one that has been modified in a way that, for instance, enhances its properties or decreases undesirable side effects, but that still retains the desired botulinum toxin activity. The botulinum toxin may be any of the botulinum toxin complexes produced by the bacterium, as described above. Alternatively, the botulinum toxin may be a toxin prepared using recombinant or synthetic chemical techniques (e.g. a recombinant peptide, a fusion protein, or a hybrid neurotoxin, as prepared from subunits or domains of different botulinum toxin serotypes (see U.S. Pat. No. 6,444,209, for instance)). The botulinum toxin may also be a portion of the overall molecule that has been shown to possess the necessary botulinum toxin activity, and in such case may be used per se or as part of a combination or conjugate molecule, for instance a fusion protein. Additionally, the botulinum toxin may be in the form of a botulinum toxin precursor, which may itself be non-toxic, for instance a nontoxic zinc protease that becomes toxic on proteolytic cleavage.

This invention also contemplates the general use of combinations and mixtures of botulinum toxins, although due to their differing nature and properties, mixtures of botulinum toxin serotypes are not generally administered at this time in the health-care or cosmetic industries.

Compositions of this invention are preferably in the form of products to be applied to the skin or epithelium of subjects or patients, i.e. humans or other mammals in need of the particular treatment. The term "in need" is meant to include both pharmaceutical or health-related needs, for example, treating conditions involving undesirable facial muscle spasms, as well as cosmetic and subjective needs, for example, altering or improving the appearance of facial tissue. In general the compositions are prepared by mixing the botulinum toxin with the carrier, and usually with one or more additional pharmaceutically acceptable carriers or excipients. In their simplest form they may contain a simple aqueous pharmaceutically acceptable carrier or diluent, such as buffered saline. However, the compositions may contain other ingredients typical in topical pharmaceutical or cosmeceutical compositions, including a dermatologically or pharmaceutically acceptable carrier, vehicle or medium, (i.e. a carrier, vehicle or medium that is compatible with the tissues to which they will be applied.) The term "dermatologically or pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology. The compositions also may include a quantity of a small anion, preferably a polyvalent anion, for example, phosphate, aspartate, or citrate.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain, in addition to the botulinum toxin and carrier, other ingredients typically used in such products, such as antimicrobials, moisturizers and hydration agents, penetration agents, preservatives, emulsifiers, natural or synthetic oils, solvents, surfactants, detergents, emollients, antioxidants, fragrances, fillers, thickeners, waxes, odor absorbers, dyestuffs, coloring agents, powders, and optionally including anesthetics, anti-itch additives, botanical extracts, conditioning agents, darkening or lightening agents, glitter, humectants, mica, minerals, polyphenols, silicones or derivatives thereof, sunblocks, vitamins, and phytomedicinals.

In particularly preferred embodiments, the compositions include gelling agents and/or viscosity-modifying agents. These agents are generally added to increase the viscosity of the composition, so as to make the application of the composition easier and more accurate. Additionally, these agents help to prevent the aqueous botulinum toxin/carrier solution from drying out, which tends to cause a decrease in the activity of the botulinum toxin. Particularly preferred agents are those that are uncharged and do not interfere with the botulinum toxin activity or the efficiency of the toxin-carrier complexes in crossing skin. The gelling agents may be certain cellulose-based gelling agents, such as hydroxypropylcellulose (HPC) for example. In some embodiments, the botulinum toxin/carrier complex is formulated in a composition having 2-4% HPC. Alternatively, the viscosity of a solution containing a botulinum toxin/carrier complex may be altered by adding polyethylene glycol (PEG). In other embodiments, the botulinum toxin/carrier solution is combined with pre-mixed viscous agents, such as CETAPHIL® moisturizer.

The compositions of this invention may optionally include partitioning agents. As used herein, a "partitioning agent" is any substance or additive that has the property of preventing or minimizing unwanted or uncontrolled aggregation of the botulinum toxin with the carriers of this invention. Partitioning agents may be useful, for example, when a concentrated botulinum toxin solution must be employed due to volume constraints. In these cases, the partitioning agent keeps the botulinum toxin dispersed, thereby preventing aggregation of the toxin that would otherwise occur without the partitioning agent. Generally, a partitioning agent is (1) non-irritating, (2) does not destroy the botulinum toxin, (3) does not confer any increase in permeability, (4) affords reliable and stable particle sizes, (5) is uncharged, and (6) does not interfere with complexes of the toxin and the transdermal carrier. An example of a suitable partitioning agent is ethanol (EtOH). In preferred embodiments, the EtOH is less than 20% of the composition, and most preferably, less than 5% of the composition.

By way of example, if volume constraints require reconstituting 100 U of botulinum toxin in 0.5 ml of solution, rather than 2.5 ml, one typically observes that the botulinum toxin will exhibit undesirable aggregation, and thus lowered activity. However, by adding 1% EtOH as a dispersing agent, fully activity is maintained even after 24 hours at this concentration. As another example, BOTOX® at 1.0 ml 0.9% NaCl reconstitution has full activity, while reconstitution at 0.5 ml in 1% and 5% EtOH plus 0.9% NaCl produces solutions with full activity.

In certain embodiments of this invention, oligo- or polyanion bridges are added to the botulinum toxin compositions to improve the complexation of the toxin with a positively charged backbone carrier. As is well known in the art, botulinum toxin is actually a complex of different proteins, some of which are positively charged, and some of which are negatively charged. Because the exact distribution of the components of the toxin varies depending on the source of the toxin, it may be that botulinum toxin from certain sources has a lower propensity for complexation with the positively charged backbones described herein. However, one aspect of this invention is the discovery that by adding an oligo- or polyanion bridge to such botulinum toxins, the efficiency and efficacy of topical administration is increased dramatically. Suitable examples of such oligo-/polyanion bridges include sodium phosphate (5%), PBS, or 5% poly-L-aspartate (e.g., with a MW of 3000).

Compositions according to this invention may be in the form of controlled-release or sustained-release compositions, wherein the botulinum toxin and the carrier are encapsulated or otherwise contained within a material such that they are released onto the skin in a controlled manner over time. The botulinum toxin and carrier may be contained within matrixes, liposomes, vesicles, microcapsules, microspheres and the like, or within a solid particulate material, all of which is selected and/or constructed to provide release of the botulinum toxin over time. The botulinum toxin and the carrier may be encapsulated together (e.g., in the same capsule) or separately (in separate capsules).

Using the compositions described herein, botulinum toxin can be delivered to muscles underlying the skin, or to glandular structures within the skin, in an effective amount to produce paralysis, produce relaxation, alleviate contractions, prevent or alleviate spasms, reduce glandular output, or other desired effects. Local delivery of the botulinum toxin in this manner could afford dosage reductions, reduce toxicity and allow more precise dosage optimization for desired effects relative to injectable or implantable materials.

The compositions of the invention are applied so as to administer an effective amount of the botulinum toxin. The term "effective amount" as used herein means an amount of a botulinum toxin as defined above that is sufficient to produce the desired muscular paralysis or other biological or aesthetic effect, but that implicitly is a safe amount, i.e. one that is low enough to avoid serious side effects. Desired effects include the relaxation of certain muscles with the aim of, for instance, decreasing the appearance of fine lines and/or wrinkles, especially in the face, or adjusting facial appearance in other ways such as widening the eyes, lifting the corners of the mouth, or smoothing lines that fan out from the upper lip, or the general relief of muscular tension. The last-mentioned effect, general relief of muscular tension, can be effected in the face or elsewhere. The compositions of the invention may contain an appropriate effective amount of the botulinum toxin for application as a single-dose treatment, or may be more concentrated, either for dilution at the place of administration or for use in multiple applications. Through the use of the positively charged carriers of this invention, a botulinum toxin can be administered transdermally to a subject for treating conditions such as undesirable facial muscle or other muscular spasms, hyperhidrosis, acne, or conditions elsewhere in the body in which relief of muscular ache or spasms is desired. The botulinum toxin is administered topically for transdermal delivery to muscles or to other skin-associated structures. The administration may be made, for example, to the legs, shoulders, back (including lower back), axilla, palms, feet, neck, groin, dorsa of the hands or feet, elbows, upper arms, knees, upper legs, buttocks, torso, pelvis, or any other part of the body where administration of the botulinum toxin is desired.

Administration of botulinum toxin formulations according to the invention may also be carried out to treat other conditions, including treating of neurologic pain, prevention or reduction of migraine headache or other headache pain, prevention or reduction of acne, prevention or reduction of dystonia or dystonic contractions (whether subjective or clinical), prevention or reduction of symptoms associated with subjective or clinical hyperhidrosis, reducing hypersecretion or sweating, reducing or enhancing immune response, or treatment of other conditions for which administration of botulinum toxin by injection has been suggested or performed.

Administration of botulinum toxin or other therapeutic proteins described herein may also be carried out for immunization-related purposes. Surprisingly, administration of botulinum toxin described herein may be carried out to reduce immune responses. More specifically, this invention allows a botulinum toxin to be delivered by an altered route of administration, thereby changing the complex antigen presentation of the agent. In this way, the invention may be useful to reduce immune response to antigens to botulinum toxin, and to facilitate repeat administration without immune-related reduction in activity. Alternatively, the complex can be prepared and applied topically to enhance an immune response, for example to provide immunizations respecting various proteins, for example, for childhood immunizations without injections. For use in connection with immune-related activity, an "effective amount" refers to an amount of the botulinum toxin sufficient to allow a subject to mount an immune response to the botulinum toxin after application or a series of applications of it.

Most preferably, the compositions are administered by or under the direction of a physician or other health care professional. They may be administered in a single treatment or in a series of periodic treatments over time. For transdermal delivery of botulinum toxin for the purposes mentioned above, a composition as described above is applied topically to the skin at a location or locations where the effect is desired. In embodiments were an aqueous botulinum toxin/carrier solution is applied directly to the skin, it is preferable to cover the treated area (e.g., with CETAPHIL® moisturizer) or occlude the treated area with a barrier (e.g., Telfa), in order to prevent the solution from drying out, which would lead to a decrease in toxin activity. Because of its nature, most preferably the amount of botulinum toxin applied should be applied with care, at an application rate and frequency of application that will produce the desired result without producing any adverse or undesired results. Accordingly, for instance, topical compositions of the invention should be applied at a rate of from about 1 U to about 20,000 U, preferably from about 1 U to about 10,000 U botulinum toxin per $cm^2$ of skin surface. Higher dosages within these ranges could preferably be employed in conjunction with controlled release materials, for instance, or allowed a shorter dwell time on the skin prior to removal.

Proper preparation of the skin surface prior to the application of the botulinum toxin/carrier composition is important for maintaining the efficacy of the solution. For example, the introduction of surfactants on the surface of the skin for the purpose of cleaning off surface oils on the skin prior to application is surprisingly counterproductive, because the surfactants appear to destroy the activity of the botulinum toxin. This occurs even if the skin is subsequently washed with water several times before application of the botulinum toxin/carrier solution. Even extremely gentle surfactants, such as those found in baby wipes, appear to cause this phenomenon. Accordingly, in preferred methods of administering the compositions of this invention, the skin is pre-cleaned using water alone. Washing with only water also appears to improve the transdermal transport of the botulinum toxin moderately.

Additionally, the skin may be stripped to reduce the stratum corneum layer prior to application of the botulinum toxin/carrier complex. In principle, the process of stripping the skin should lead to enhanced efficiency of transdermal transport of botulinum toxin. However, the method used to strip the skin is important. For example, acetone-mediated reduction of the stratum corneum layer in humans or animals appears to reduce the activity of subsequently applied botulinum toxin. In contrast, tape stripping (i.e., applying tape on the surface of the skin and then removing the tape) appears to allow deeper penetration of the botulinum toxin and dosage reduction in both mouse models and humans. It is presumed that abrasion of the skin surface (e.g., via the use of abrasive pads) would cause a similar effect as tape stripping.

This invention also comprises devices for transdermal transmission of a composition that contains botulinum toxin and a carrier that has a positively charged backbone with attached branching groups as defined herein. Such devices may be as simple in construction as a skin patch, or may be more complicated devices that include means for dispensing and monitoring the dispensing of the composition, and optionally means for monitoring the condition of the subject (e.g., monitoring the reaction of the subject to the substances being dispensed).

It should be noted that the choice of materials for the construction of the device is important. Preferred materials for the construction of delivery devices are those that do not lead to a loss of activity of the botulinum toxin/carrier solution, either through degradation or unwanted adsorption of the botulinum toxin on a surface of the device. Such undesired behavior has been observed, for example, when botulinum toxin/carrier in an aqueous solution contacts polypropylene surfaces, but not when the botulinum toxin/carrier solution contacts polyvinyl chloride (PVC) surfaces.

Generally, the compositions can be pre-formulated and/or pre-installed in a device or can be prepared later, for example using a kit that houses the two ingredients (botulinum toxin and carrier) separately but provides means for combining them at or prior to the time of application. The amount of carrier molecule or the ratio of it to the botulinum toxin will depend on which carrier is chosen for use in the composition in question. The appropriate amount or ratio of carrier molecule in a given case can readily be determined, for example, by conducting one or more experiments, such as those described below.

In general, the invention also comprises a method for administering a botulinum toxin to a subject or patient in need thereof. The method includes comprising topically administering an effective amount of the botulinum toxin in conjunction with a carrier having a positively charged backbone with attached positively charged branching groups, as described herein. By "in conjunction with" is meant that the two components (botulinum toxin and carrier) are administered in a combination procedure, which may involve either combining them in a composition, which is subsequently administered to the subject, or administering them separately, but in a manner such that they act together to provide the requisite delivery of an effective amount of the therapeutic protein. For example, a composition containing the carrier may first be applied to the skin of the subject, followed by applying a skin patch or other device containing the botulinum toxin. The botulinum toxin may be incorporated in dry form in a skin patch or other dispensing device, while the positively charged carrier may be applied to the skin surface before application of the patch so that the two act together, resulting in the desired transdermal delivery. Thus, the two substances (carrier and botulinum toxin) act in combination or perhaps interact to form a composition or combination in situ. Accordingly, the invention also comprises a kit that includes both a device for dispensing botulinum toxin via the skin and a liquid, gel, cream or the like that contains the carrier or backbone, and that is suitable for applying to the skin or epithelium of a subject. Kits for administering the compositions of the inventions, either under direction of a health care professional or by the patient or subject, may also include a custom applicator suitable for that purpose.

The compositions, kits and methods of this invention allow for the delivery of a more pure botulinum toxin with higher specific activity and potentially improved pharmacokinetics. In addition, the carrier can act as a stabilizer, reducing the need for foreign accessory proteins (e.g., human serum albumin ranging from 400-600 mg or recombinant serum albumin ranging from 250-500 mg) and/or polysaccharide stabilizers, and can afford beneficial reductions in immune responses to the botulinum toxin. In addition, the compositions are suitable for use in physiologic environments with pH ranging from about 4.5 to about 6.3, and may thus have such a pH. The compositions according to this invention may be stored either at room temperature or under refrigerated conditions.

The following are representative examples of the invention. They demonstrate delivery of functional botulinum neurotoxin complexes across skin without requiring covalent modification of the neurotoxin to be delivered.

EXAMPLES

Example 1

Transport of a Botulinum Toxin In Vivo Using a Revance Peptidyl Carrier

This experiment demonstrates the use of a peptidyl carrier to transport a large complex containing an intact labeled protein botulinum toxin across intact skin after a single time administration relative to controls.

Backbone Selection:

The positively charged backbone was assembled by conjugating -$Gly_3Arg_7$ (SEQ ID NO:5) to polylysine (MW 112,000) via the carboxyl of the terminal glycine to free amines of the lysine side chains at a degree of saturation of 18% (i.e., 18 out of each 100 lysine residues is conjugated to a -$Gly_3Arg_7$ (SEQ ID NO:5)). The modified backbone was designated "KNR". The control polycation was unmodified polylysine (designated "K", Sigma Chemical Co., St. Louis, Mo.) of the same size and from the same lot.

Therapeutic Agent:

BOTOX® brand of botulinum toxin A (Allergan) was selected for this experiment. It has a molecular weight of approximately 150,000.

Preparation of Samples:

The botulinum toxin was reconstituted according to the manufacturer's instructions. An aliquot of the protein was biotinylated with a calculated 12-fold molar excess of sulfo-NHS-LC biotin (Pierce Chemical). The labeled product was designated "Btox-b."

In each case, an excess of polycation was employed to assemble a final complex that has an excess of positive charge as in delivery of highly negative large nucleotide complexes. A net neutral or positive charge prevents repulsion of the protein complex from highly negative cell surface proteoglycans and extracellular matrix. Btox-b dose was standardized across all groups, as was total volume and final pH of the composition to be applied topically. Samples were prepared as follows:

Group labeled "JMW-7": 2.0 units of Btox-b per aliquot (i.e. 20 U total) and peptidyl carrier KNR at a calculated MW ratio of 4:1 were mixed to homogeneity and diluted to 200 microliters with phosphate buffered saline. The resulting composition was mixed to homogeneity with 1.8 ml of CETAPHIL® cream and aliquoted in 200 microliter portions.

Group labeled "JMW-8": 2.0 units of Btox-b per aliquot (i.e. 20 U total) and K at a MW ratio of 4:1 were mixed to homogeneity and diluted to 200 microliters with phosphate buffered saline. The resulting composition was mixed to homogeneity with 1.8 ml of CETAPHIL® and aliquoted in 200 microliter portions.

Animal Experiments to Determine Transdermal Delivery Efficiencies after Single Time Treatment with Peptidyl Carriers and Labeled Btox:

Animals were anesthetized via inhalation of isoflurane during application of treatments. After being anesthetized, C57 black 6 mice (n=4 per group) underwent topical application of a metered 200 microliter dose of the appropriate treatment applied to the cranial portion of dorsal back skin (selected because the mouse cannot reach this region with mouth or limbs). Animals did not undergo depilation. At 30 minutes after the initial treatment, mice were euthanized via inhalation of $CO_2$, and treated skin segments were harvested at full thickness by blinded observers. Treated segments were divided into three equal portions; the cranial portion was fixed in 10% neutral buffered formalin for 12-16 hours then stored in 70% ethanol until paraffin embedding. The central portion was snap-frozen and employed directly for biotin visualization by blinded observers as summarized below. The treated caudal segment was snap frozen for solubilization studies.

Biotin visualization was conducted as follows. Briefly, each section was immersed for 1 hour in NeutrAvidin® buffer solution. To visualize alkaline phosphatase activity, cross sections were washed in saline four times then immersed in NBT/BCIP (Pierce Scientific) for 1 hour. Sections were then rinsed in saline and photographed in entirety on a Nikon E600 microscope with plan-apochromat lenses.

Data Handling and Statistical Analysis:

Total positive staining was determined by blinded observer via batch image analysis using Image Pro Plus software (Media Cybernetics, Silver Spring, Md.) and was normalized to total cross-sectional area to determine percent positive staining for each. Mean and standard error were subsequently determined for each group with analysis of significance at 95% confidence in one way ANOVA repeated measures using Statview software (Abacus, Berkeley, Calif.).

Results:

The mean cross-sectional area that was positive for biotinylated botulinum toxin was reported as percent of total area after single-time topical administration of Btox-b with either KNR ("EB-Btox") or K ("n1"). The results are presented in the following Table 1 and are illustrated in FIG. 1. In FIG. 1, the area positive for label was determined as percent of total area after three days of once daily treatment with "EB-Btox" which contained Btox-b and the peptidyl carrier KNR and "n1", which contained Btox-b with polycation K as a control. Mean and standard error are depicted for each group.

TABLE 1

Mean and standard error for labeled botulinum toxin area as percent of total cross-section after single time topical administration of Btox-b with KNR (JMW-7) or K (JMW-8) for 30 minutes

| Group | Mean | Std. Error |
|---|---|---|
| JMW-7 | 33 | 5.333334 |
| JMW-8 | 8.666667 | 0.333334 |

P = 0.0001 (Significant at 99%)

Example 2

Therapeutic Efficacy of a Topical Botulinum Toxin Preparation with a Peptidyl Carrier Example 1 demonstrated that the peptidyl transdermal carrier allowed efficient transfer of botulinum toxin after topical administration in a murine model of intact skin. However, this experiment did not indicate whether the complex protein botulinum toxin was released in a functional form after translocation across skin. The following experiment was thus constructed to evaluate whether botulinum toxin can be therapeutically delivered across intact skin as a topical agent using this peptidyl carrier (again, without covalent modification of the protein).

The positively charged backbone was again assembled by conjugating -Gly$_3$Arg$_7$ (SEQ ID NO:5) to polylysine (MW 112,000) via the carboxyl of the terminal glycine to free amines of the lysine side chains at a degree of saturation of 18% (i.e., 18 out of each 100 lysine residues is conjugated to a -Gly$_3$Arg$_7$ (SEQ ID NO:5)). The modified backbone was designated "KNR". Control polycation was unmodified polylysine (designated "K", Sigma Chemical Co., St. Louis, Mo.) of the same size and from the same lot. The same botulinum toxin therapeutic agent was used as in Example 1, and was prepared in the same manner. Samples were prepared as follows:

Group labeled "JMW-9": 2.0 units of botulinum toxin per aliquot (i.e. 60 U total) and peptidyl carrier KNR at a calculated MW ratio of 4:1 were mixed to homogeneity and diluted to 600 microliters with phosphate buffered saline. The resulting composition was mixed to homogeneity with 5.4 ml of CETAPHIL® and aliquoted in 200 microliter portions.

Group labeled "JMW-10": 2.0 units of botulinum toxin per aliquot (i.e. 60 U total) and K at a MW ratio of 4:1 were mixed to homogeneity and diluted to 600 microliters with phosphate buffered saline. The resulting composition was mixed to homogeneity with 5.4 ml of CETAPHIL® and aliquoted in 200 microliter portions.

Group labeled "JMW-11": 2.0 units of botulinum toxin per aliquot (i.e. 60 U total) without polycation was diluted to 600 microliters with phosphate buffered saline. The resulting composition was mixed to homogeneity with 5.4 ml of CETAPHIL® and aliquoted in 200 microliter portions.

Animal Experiments to Determine Therapeutic Efficacy after Single Time Treatment with Peptidyl Carriers and Botulinum Toxin:

Animals were anesthetized via inhalation of isoflurane during application of treatments. After being anesthetized, C57 black 6 mice (n=4 per group) underwent topical application of metered 400 microliter dose of the appropriate treatment applied uniformly from the toes to the mid-thigh. Both limbs were treated, and treatments were randomized to either side. Animals did not undergo depilation. At 30 minutes after the initial treatment, mice were evaluated for digital abduction capability according to published digital abduction scores for foot mobility after botulinum toxin administration [Aoki, K R. *A comparison of the safety margins of botulinum neurotoxin serotypes A, B, and F in mice*. Toxicon. 2001 December; 39(12): 1815-20]. Mouse mobility was also subjectively assessed.

Data Handling and Statistical Analysis:

Digital abduction scores were tabulated independently by two blinded observers. Mean and standard error were subsequently determined for each group with analysis of significance at 95% confidence in one way ANOVA repeated measures using Statview software (Abacus, Berkeley, Calif.).

Figure 2:
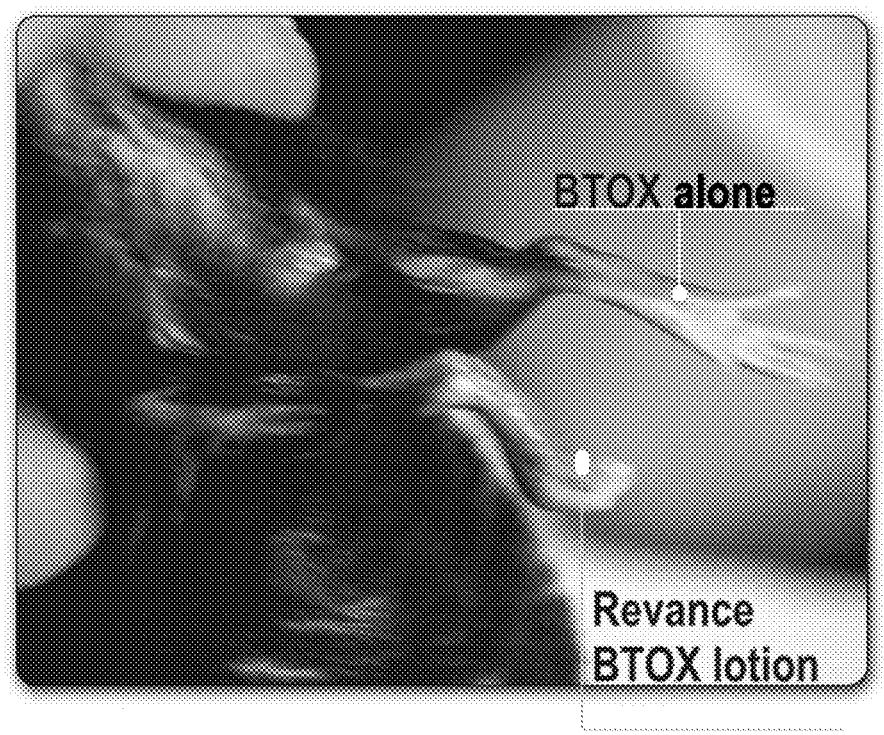
FIG. 2 is a photograph depicting the state of the hind limbs of a mouse in which the area of one limb was treated with a composition of the invention and the area of the other was treated with another botulinum toxin-containing composition that did not contain a carrier according to the invention.
Figure 5:
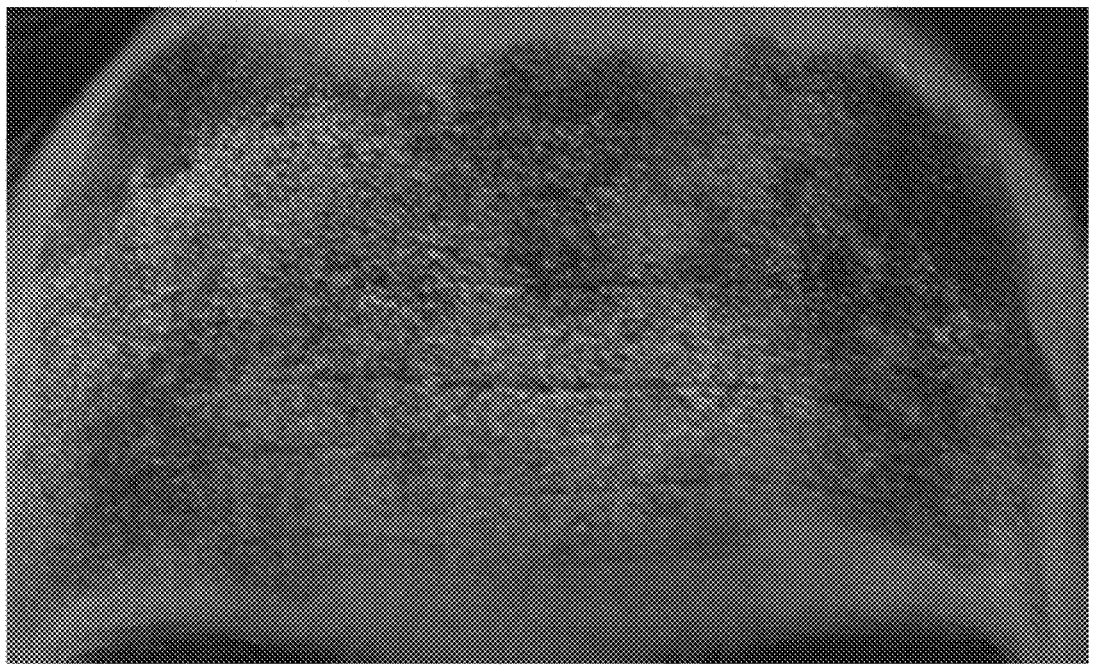
FIG. 5 shows a photograph depicting Minor's starch/iodine test performed on subject's forehead prior to treatment.

Results:

Mean digital abduction scores after single-time topical administration of botulinum toxin with KNR ("JMW-9"), K ("JMW-10") or diluent without polycation ("JMW-11"), are presented in Table 2 and illustrated in the representative photomicrograph of FIG. 2 below. The peptidyl carrier KNR afforded statistically significant functional delivery of the botulinum toxin across skin relative to both controls, which were comparable to one another. Additional independent repetitions (total of three independent experiments all with identical conclusions in statistically significant paralysis from topical botulinum toxin with KNR but not controls) of the present experiment confirmed the present findings and revealed no significant differences between topical botulinum toxin with or without K (i.e. both controls). Interestingly, the mice consistently ambulated toward a paralyzed limb (which occurred in 100% of treated animals and 0% of controls from either control group). As shown in FIG. 2, a limb treated with botulinum toxin plus the control polycation polylysine or with botulinum toxin without polycation ("toxin alone") can mobilize digits (as a defense mechanism when picked up), but the limbs treated with botulinum toxin plus the peptidyl carrier KNR (Revance's botulinum formulation) could not be moved.

TABLE 2

Digital abduction scores 30 minutes after single-time topical application of botulinum toxin with the peptidyl carrier KNR ("JMW-9"), with a control polycation K ("JMW-10"), or alone ("JMW-11")

| Group | Mean | Std. Error |
|---|---|---|
| JMW-9 | 3.333 | 0.333 |
| JMW-10 | 0.333 | 0.333 |
| JMW-11 | 0.793 | 0.300 |

P = 0.0351 (Significant at 95%)

Conclusions:

This experiment serves to demonstrate that the peptidyl transdermal carrier can transport a therapeutically effective amount of botulinum therapeutic across skin without covalent modification of the therapeutic. The experiment also confirms that botulinum toxin does not function when applied topically in controls.

Example 3

Therapeutic Efficacy of a Topical Botulinum Toxin Preparation with a Nonpeptidyl Carrier This experiment demonstrates the performance of a nonpeptidyl carrier in the invention.

Methods:
Backbone Selection:

The positively charged backbone was assembled by conjugating -Gly$_3$Arg$_7$ (SEQ ID NO:5) to polyethyleneimine (PEI) MW 1,000,000 via the carboxyl of the terminal glycine to free amines of the PEI side chains at a degree of saturation of 30% (i.e., 30 out of each 100 lysine residues is conjugated to a -Gly$_3$Arg$_7$ (SEQ ID NO:5)). The modified backbone was designated "PEIR" to denote the large nonpeptidyl carrier. Control polycation was unmodified PEI (designated "PEI", Sigma Chemical Co., St. Louis, Mo.) of the same size and from the same lot. The same botulinum toxin therapeutic agent was used as in Example 1.

Botulinum toxin was reconstituted from the BOTOX® product according to the manufacturer's instructions. In each case, an excess of polycation was employed to assemble a final complex that had an excess of positive charge as in delivery of highly negative large nucleotide complexes. A net neutral or positive charge prevents repulsion of the protein complex from highly negative cell surface proteoglycans and extracellular matrix. The botulinum toxin dose was standardized across all groups as was total volume and final pH of the composition to be applied topically. Samples were prepared as follows:

Group labeled "AZ": 2.0 units of botulinum toxin per aliquot (i.e. 60 U total) and the nonpeptidyl carrier PEIR in ultrapure form at a calculated MW ratio of 5:1 were mixed to homogeneity and diluted to 600 microliters with phosphate buffered saline. The resulting composition was mixed to homogeneity with 5.4 ml of CETAPHIL® and aliquoted in 200 microliter portions.

Group labeled "BA": 2.0 units of botulinum toxin per aliquot (i.e. 60 U total) and PEI at a charge ratio of 5:1 were mixed to homogeneity and diluted to 600 microliters with phosphate buffered saline. The resulting composition was mixed to homogeneity with 5.4 ml of CETAPHIL® and aliquoted in 200 microliter portions.

Animal Experiments to Determine Therapeutic Efficacy after Single Time Treatment.

Animals were anesthetized via inhalation of isoflurane during application of treatments. After being anesthetized, C57 black 6 mice (n=3 per group) underwent topical application of metered 400 microliter dose of the appropriate treatment applied uniformly from the toes to the mid-thigh. Both limbs were treated, and treatments were randomized to either side. Animals did not undergo depilation. At 30 minutes after the initial treatment, mice were evaluated for digital abduction capability according to published digital abduction scores for foot mobility after botulinum toxin administration [Aoki, K R. *A comparison of the safety margins of botulinum neurotoxin serotypes A, B, and F in mice*. Toxicon. 2001 December; 39(12): 1815-20]. Mouse mobility was also subjectively assessed.

Data Handling and Statistical Analysis:

Digital abduction scores were tabulated independently by two blinded observers. Mean and standard error were subsequently determined for each group with analysis of significance at 95% confidence in one way ANOVA repeated measures using Statview software (Abacus, Berkeley, Calif.).

Results:

Mean digital abduction scores after single-time topical administration of botulinum toxin with ultrapure PEIR ("AZ"), or control polycation PEI ("BA"), are presented in Table 3 and repetition presented as Table 4 (single independent repetition for this experiment). The nonpeptidyl carrier PEIR afforded statistically significant functional delivery of botulinum toxin across skin relative to controls. As before, animals were observed to walk in circles toward the paralyzed limbs.

TABLE 3

Digital abduction scores 30 minutes after single-time topical administration of BOTOX ® with ultrapure PEIR ("AZ"), or control polycation PEI ("BA"). Mean and standard error are presented.

| Group | Mean | Std. Error |
| --- | --- | --- |
| BA | 0.833 | 0.307 |
| AZ | 3.917 | 0.083 |

P = 0.0002 (Significant at 99%)

TABLE 4

Digital abduction scores 40 minutes after single-time topical administration of BOTOX ® with ultrapure PEIR ("AZ1"), or control polycation PEI ("BA1"). Mean and standard error are presented.

| Group | Mean | Std. Error |
| --- | --- | --- |
| BA1 | 0.333 | 0.211 |
| AZ1 | 3.833 | 0.167 |

P = 0.0001 (Significant at 99%)

Conclusions:

This experiment demonstrated that the nonpeptidyl transdermal carrier can transport therapeutic doses of botulinum toxin across skin without prior covalent modification of the botulinum toxin. These findings complement those with peptidyl transfer agents. The option of using a nonpeptidyl or a peptidyl carrier to achieve the therapeutic effect will allow tailoring to specific circumstances, environments, and methods of application and add to the breadth of the transdermal delivery platform of this invention.

Example 4

Therapeutic Efficacy of a Topical Botulinum Toxin Preparation with Peptidyl Carrier for Forehead Hyperhidrosis and Wrinkles This experiment demonstrates that botulinum toxin can be therapeutically delivered across intact skin as a topical agent using this peptidyl carrier for the treatment of forehead hyperhidrosis and wrinkles on human subjects.

Experimental Procedure for Forehead Hyperhidrosis and Wrinkles Study:

Baseline and post-treatment photographs of the subject's forehead were taken on a blue background using a Nikon D70 camera with Nikon TTL Macro-speedlight SB29s flash (Nikon, Inc. USA).

Baseline and post-treatment videos of the subject's forehead were taken on a blue background using a Sony Digital Handycam camcorder.

Minor's starch/iodine test was performed to visualize sweat production using 10% topical povidone iodine solution (Walgreen Co., Deerfield, Ill.) and Kingsford's 100% corn starch (ACH Food Companies, Inc., Memphis, Tenn.). The subject's forehead was painted with an iodine solution using sterile cotton balls (Johnson & Johnson Consumer Product Company, Skillman, N.J.), and then allowed to dry completely. The area was lightly dusted with starch powder using sterile cotton balls. The sweat was induced with physical activity at ambient room temperature. Dark blue-black spots appeared as the sweat dissolved the iodine and reacted with starch powder. Baseline and post-treatment photographs of iodine-starch test were taken on a blue background using a Nikon D70 camera with Nikon TTL Macro-speedlight SB29s flash. The subject's forehead was cleansed with 70% EtOH and then deionized water.

The subject's predefined treatment area on the forehead was prepared by non-invasive tape stripping method for stratum corneum prior to treatment application. Precut tape was applied to the treatment area with firm pressure for few seconds. It was removed rapidly by pulling on one corner of the tape. The second tape was carefully applied to the same area immediately after the first tape was removed. Tape-stripping was repeated 3-5 times.

Treatment Preparation:

The BOTOX® reconstituting solution of sterile 0.9% sodium chloride (Abbott Laboratories, North Chicago, Ill.) plus 5% EtOH plus 5% short chained polyaspartate solution labeled A-3C (Donlar BioPolymer, Inc. Bedford Park, Ill.) was prepared (i.e., for every 1.0 milliliter solution, 900 microliters of sterile 0.9% sodium chloride plus 50 microliters of 100% EtOH plus 50 microliters of short chained polyaspartate solution). Kn21T was prepared at 1 milligram/milliliter concentration with 0.9% sodium chloride plus 5% EtOH (i.e., 500 microliters of Kn21T was aliquoted and 25 microliters of 100% EtOH was added). As used herein, Kn21T refers to a positively charged polylysine backbone having a molecular weight of 21,000 and TAT branching groups. 100 units of BOTOX® (Allergan, Irvine, Calif.) was reconstituted with 1.0 milliliters of reconstituting solution using sterile 3 ml latex free syringe with $18_G 11/2$ (Becton Dickinson & Co., Franklin Lakes, N.J.). The reconstituted BOTOX® was carefully mixed by inversion 8 times. 200 units of BOTOX® were used for each subject. Revance's botulinum formulation was prepared with 200 units of BOTOX® and Kn21T plus 5% EtOH (i.e., 2.0 milliliters of BOTOX® was added to 500 microliters of Kn21T plus 25 microliters of 100% EtOH) and sat at room temperature for 5 minutes for the complexes to form.

The control solution was prepared with reconstituting solution and Kn21T plus 5% EtOH (i.e., 2.0 ml of reconstituting solution was added to 500 microliters of Kn21T plus 25 microliters of 100% EtOH) and kept at room temperature.

Treatment Application:

The subject reclined on a table with protective covering around the eyes, face, and upper body. The treatment was applied evenly to the subject's forehead using a pipette and massaged into the skin in circular motion with fingers while wearing powder-free, nitrile gloves. The treatment area was covered with a thin layer of CETAPHIL® moisturizing cream (Galderma, Fort Worth, Tex.) and incubated for 60 minutes. After 60 minute incubation, the treatment was removed with sterile gauze pads. The gauze pads and gloves were discarded in a biohazard bag.

Results:

FIG. 3 depicts significant reduction in wrinkle length depth and width after topical treatment with Peptidyl carrier and botulinum combination. This experiment confirms that topically applied botulinum toxin, when combined with transdermal carrier, can afford significant muscular paralysis to afford a cosmetic effect. FIG. 4 is a MIKROSIL cast of the treated skin (A) versus untreated skin (B). Wrinkles are visible on the cast of the untreated skin.

Figure 6A:
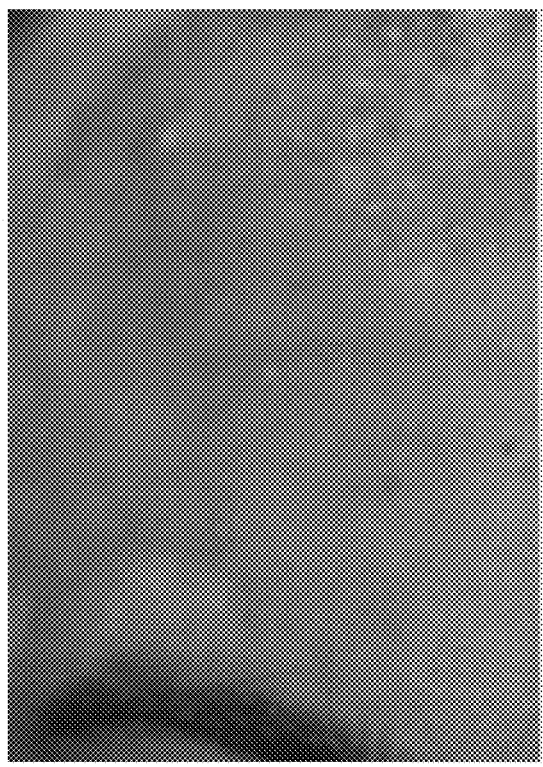
FIGS. 6A-6D.
Figure 6B:
Figures 6C, 6D:
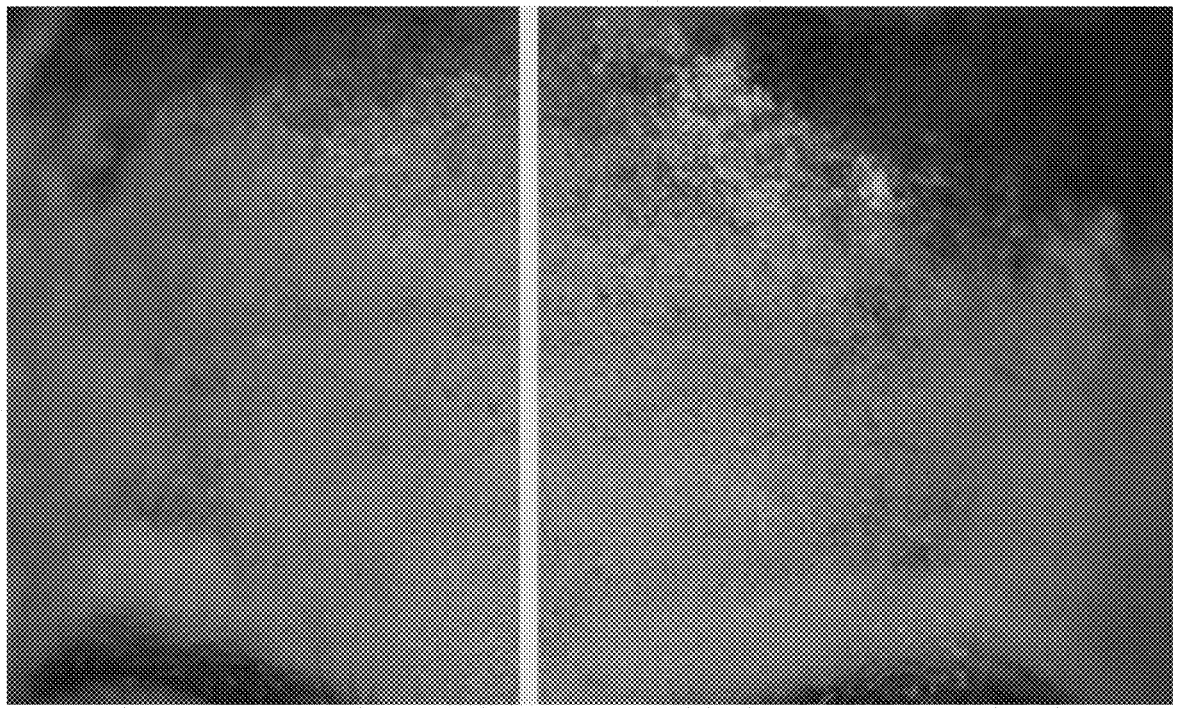

FIGS. 6A-6D show the results of the Minor's starch/iodine test. FIGS. 6A and 6B show photos taken two minutes after application, with FIG. 6A corresponding to the side treated with Revance's botulinum formulation and FIG. 6B corresponding to the side treated with a control formulation containing Kn21T carrier alone. FIGS. 6C and 6D are the same as FIGS. 6A and 6B, respectively, except taken at four minutes. Note the more pronounced coloration on the control formulation side, indicating that the skin on that side is secreting more sweat. Also note that the sweating starts earlier on the untreated side.

Conclusions:

This example demonstrates that topically applied complexes of botulinum toxin can afford significant aesthetic benefit in reducing fine and coarse wrinkles. This transepithelial effect further confirms that muscle paralysis can be accomplished with appropriate carriers after topical application of botulinum toxin complexes such as those disclosed herein. This example thus indicates that topical application of botulinum toxin can lead to relief from muscle spasms such as blepharospasm or torticollis as well as relief of muscle spasm-related pain such as lower back pain.

Example 5

Therapeutic Efficacy of a Topical Botulinum Toxin Preparation with Peptidyl Carrier for Axillary Hyperhidrosis This experiment demonstrates whether botulinum toxin can be therapeutically delivered across intact skin as a topical agent using this peptidyl carrier for the treatment of axillary hyperhidrosis on human subjects (n=10 axillae per group with one axilla treated and one control per patient in a randomized double-blind fashion).

Inclusion Criteria for Axillary Hyperhidrosis Study:
 Age: 18 years or older
 Healthy volunteers
 Informed consent given and signed by the volunteer
 Subject willing to follow instruction and return for follow-up visits.
 Subject has presence of pre-existing, subjective hyperhidrosis
 Subject is NOT pregnant or planning on becoming pregnant within the next 3 months
 Subject lives and/or work in San Francisco or near study area
 Subject has NOT had treatment for underarm sweating within the past 6 months
 Subject is NOT planning on having treatment for underarm sweating within the next 3 months Gravimetric Measurement Procedures:

As a part of the gravimetric measurement procedure, the subjects were first acclimated to the testing area. Specifically, each subject sat for 15 minutes at a room temperature of 72-77° F. in the resting position.

Axillae Preparation:

(Powder-free, nitrile gloves were worn for the following procedures.) The subject changed into disposable cape and bra (if a woman) or took off all upper body garments (if a man) so as to expose both of the axillae fully. The dose area was predetermined to be the area covered by hair bearing skin, plus an area extending 1 cm beyond the hair bearing skin at each axilla. The dose area was cleaned with a pre-wet sterile gauze pad from a 50 ml conical tube by wiping with 5 long strokes from top to bottom in the same direction using one side of the gauze. This step was repeated three more times with a clean pre-wet gauze pad each time while being careful not to irritate or abrade the skin. The gauze pads were discarded in the trash. The same wash procedure was repeated for the other axilla. The axilla was dried with dry sterile gauze by using firm padding motion from top to bottom of the axilla while being careful not to irritate or abrade the skin. Then, the axilla was further dried by placing a filter paper under the axillary crease and allowing the filter to dwell in the test site for 5 minutes following the procedure for gravimetric assessment. The patient sat with their arms against his/her body in a resting position. The filter papers were discarded in the trash. The subject was allowed to rest for 1 minute without axilla manipulation prior to the first gravimetric assessment.

Sweat Production Measurement (Gravimetric Measurement):

(A new pair of powder-free, nitrile gloves was donned prior to these measurements). The subject held his or her hands together at the back of head to expose axillae fully, while being partially reclined (about 45 degrees). A pre-weighed filter paper was removed from a conical storage tube and placed under the subject's axilla with the tip of the filter aligning with the center of axillary crease line. The filter paper held in place by using fingers while the subject relaxed arms to the side of the body. The subject sat with both arms held tightly against his/her trunk for five minutes. The timing started when the filter papers were securely placed under both of the axillae. Both axillae were measured simultaneously. After 5 minutes, the filter papers were removed from the axillae and placed back into the same respective conical tubes. The filter paper placed first was removed first. The caps of the conical tubes were screwed tightly to prevent the evaporation of the sweat from the tube. The sweat production was repeated two more times at one-minute intervals.

Minor's Starch/Iodine Test:

The subject held his/her hands together at the back of head to expose the axillae fully. The iodine solution was painted onto the axilla area predetermined as before with a sterile gauze pad and allowed to air-dry. When the iodine had completely dried, a thin layer of starch was padded onto the area covered by iodine with cotton balls. The iodine was allowed to air-dry before the application of starch in order to reduce false positive and background. The subject then sat with both arms held tightly against his/her trunk. After 5 minutes, the subject raised his/her arms and held hands together at the back of head to expose axillae fully. Photographs of each axilla with left and right axilla and the date clearly labeled were taken. The axillae were cleaned with 70% EtOH and then with sterile deionized water.

Treatment Preparation:

Kn21pr was prepared at 1 milligram/milliliter concentration with saline plus 5% EtOH (i.e., 500 microliters of Kn21pr was aliquoted and 25 microliters of 100% EtOH was added). As used herein, Kn21pr refers to a positively charged polylysine backbone with a molecular weight of 21,000 and branching groups comprising protected oligoarginine. 100 units of BOTOX® (Allergan, Irvine, Calif.) was reconstituted with 0.75 milliliters of 0.9% sodium chloride (Abbott Laboratories, North Chicago, Ill.) using sterile 3 ml latex free syringe with $18_G11/2$ (Becton Dickinson and Company, Franklin Lakes, N.J.). The reconstituted BOTOX® was carefully mixed by inversion 8 times. 200 units of BOTOX® were used for each subject. The treatment solution was prepared with 200 units of BOTOX® and Kn21pr plus 5% EtOH (i.e., 1.5 milliliters of BOTOX® was added to 500 microliters of Kn21pr plus 25 microliters of 100% EtOH) and kept at room temperature for 5 minutes to allow the complexes to form. After a 5-minute incubation period, approximately 1.0 milliliters of 4% HPC (hydroxypropylcellulose) (with 1% EtOH) was added and mixed gently and thoroughly with a small metal spatula. The homogenous treatment solution was transferred into a 3 ml syringe and syringe tip cap. (Becton Dickinson and Company, Franklin Lakes, N.J.).

The control solution was prepared with 0.9% sodium chloride and Kn21pr plus 5% EtOH (i.e., 1.5 milliliters of 0.9% sodium chloride was added to 500 microliters of Kn21pr plus 25 microliters of 100% EtOH) and sat at room temperature for five minutes. After incubation, approximately 1.0 milliliters of 4% HPC (with 1% EtOH) was added and mixed gently and thoroughly with a small metal spatula. The homogenous control solution was transferred into a 3 ml syringe and syringe tip cap.

Figure 7:
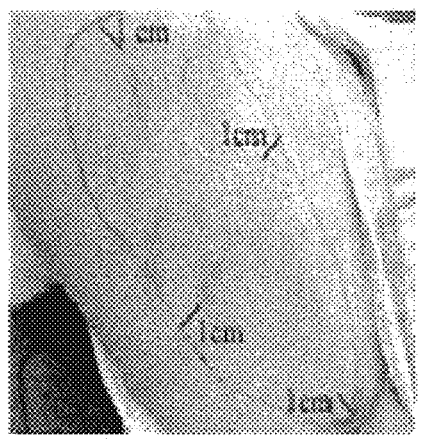
FIG. 7 shows the dose area used in the axillary hyperhidrosis studies. Note that the dose area extends one centimeter beyond the area of the skin covered by axillary hair.

Treatment Application (Wear Powder-Free, Nitrile Gloves):

The subject held his/her hands together with interlocking fingers and placed them on the back of the head to fully exposure the subject's axillae. Then, the subject reclined in a chair to an angle of about 45 degrees. As shown in FIG. 7, the dose area was visually mapped out (i.e. 1 cm beyond the hair bearing skin) for application. The dose areas were checked for dryness. The syringe tip cap was removed from the labeled syringe marked "L" for left and "R" for right, and prepared for application onto the subject's axillae. The treatment solution was spread evenly around the dose area with a syringe and massaged into the skin with fingers for 1 minute. The subject then placed his/her arms down along the side of the body and incubated for 60 minutes. After 60 minute incubation, the treatment was cleaned with sterile gauze pads. The gauze pads and gloves were discarded in a bio-hazard bag. The subject was discharged.

Figure 8A:
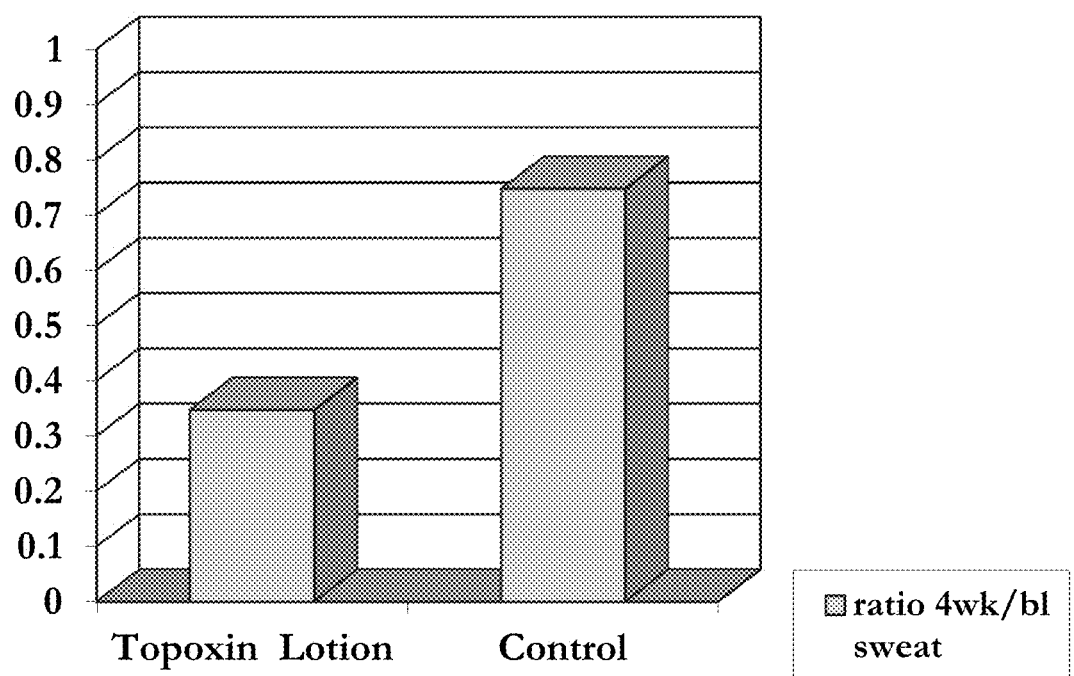
FIGS. 8A and 8B.

Results:

Revance's topical botulinum formulation reduced sweating by 65% (P=0.0137). FIG. 8A shows a comparison of sweat production at 4 weeks after treatment (randomized by side) with Kn21pr backbone alone (control) or Kn21pr backbone plus 200 U BOTOX® (ratio to baseline). Statistical analyses were performed by Wilcoxon signed ranks using NPSS with P as noted and significance at P<0.05. [n=10 subjects].

Figure 8B:
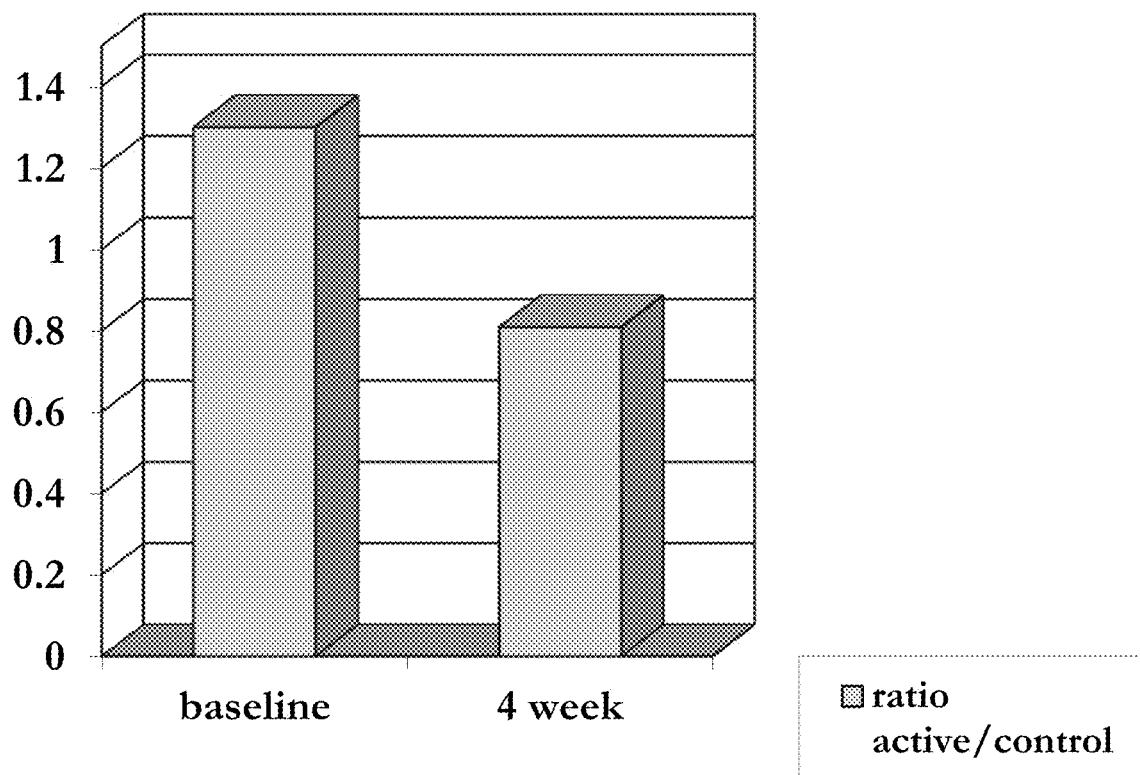

Second Comparison:

FIG. 8B shows the ratio of treatment to control compared at baseline and at 4 weeks. The figure shows sweat production (mg per 5 minutes) 4 weeks after axillary treatment (randomized by side) with Kn21pr backbone alone (control) or Kn21pr backbone plus 200 U BOTOX® (ratio of treatment to control). Statistical analyses were performed by Wilcoxon signed ranks using NPSS with P as noted and significance at P<0.05. (P=0.0195) (Pr T p=0.0217) [n=10].

FIGS. 9A-9D show photographs depicting Minor's starch/iodine test before and after treatment with Revance's botulinum formulation topically for the treatment of axillary hyperhidrosis. Starch/iodine test at baseline vs. 2 weeks is shown where right axilla was treated with Revance's botulinum formulation (Figures A and C) and left axilla was applied with the control (Figures B and D) for subject #12. These photographs illustrate typical benefits observed after treatment with carrier+botox in starch iodine. Although some crossover is observed on the control side (consistent with 25% reduction in gravimetric data), significant reductions are afforded with treatment (consistent with 65% reduction in gravimetric data on treated side).

Conclusions:

This example confirms that topical application of botulinum complexes formed according to the invention disclosed herein readily afford therapeutic benefit in reduction of sweating in a cohort of patients with hyperhidrosis—subjective or quantitative. This effect in reducing sweating has also been afforded in the forehead case presented above and in palmar/plantar application when combined with a glove to limit spread of formulation during dwell time. This transepithelial delivery of botulinum toxin complexes for therapeutic benefit confirms further that the approach can be extended to other cases where SNAP function or acetylcholine signals are crucial such as bladder dysfunction or spasm, gastrointestinal applications, or sebaceous gland secretions for smell reduction or acne prevention/treatment.

Example 6

Wipe-on Revance's Botulinum Formulation Pilot Experiment

Purpose:

To determine transport efficiency of wipe-on DYSPORT® and performance of peptidyl transdermal carriers (backbones) in a murine model.

Methods:

Study design: C57BL/6, female mice (Charles River, Wilmington, Mass.) weighing 19-20 g were used. Animals were anesthetized using isoflurane and topical application of "Revance DYSPORT® solutions" (Table 5) was performed on mouse hind limbs. After recovery, hind limb muscle weakening was scored using Digit Abduction Score (DAS) values.

TABLE 5

Description of test compounds and peptidyl transdermal carrier (backbones).

| Group | Test Compound | Backbone |
|---|---|---|
| CL | 30U DYSPORT ® (Formulation 1) | Kn21T |
| CM | 30U DYSPORT ® (Formulation 1) | Kn21Pr |
| CN | 30U DYSPORT ® (Formulation 1) | KnR |
| CO | 30U DYSPORT ® (Formulation 2) | Kn21T |
| CP | 30U DYSPORT ® (Formulation 2) | Kn21Pr |
| Control | Saline | N/A |

Test Compound Preparation:

The DYSPORT® reconstituting solution of sterile 0.9% sodium chloride (Abbott Laboratories, North Chicago, Ill.) was prepared. Backbones were prepared at 1 milligram/milliliter concentration with 0.9% sodium chloride. 500 units of DYSPORT® (Ipsen) was reconstituted with 2.5 milliliters of reconstituting solution using sterile 3 ml latex free syringe with $18_G 11/2$ (Becton Dickinson & Co., Franklin Lakes, N.J.). The reconstituted DYSPORT® was carefully mixed by inversion eight times. The Revance's botulinum formulation was prepared with 30 units of DYSPORT® and backbone (i.e. 150 microliters of DYSPORT® was added to 75 microliters of Revance carrier) in a microcentrifuge tube and sat at room temperature for 5 minutes for the complexes to form.

Topical Application:

Animals were anesthetized using 1.5% isoflurane mixed with oxygen and then injected with 0.05 ml rodent anesthetic cocktail (3.75 ml of 100 mg/ml Ketamine, 3.00 ml of 20 mg/ml Xylazine, and 23.25 ml of saline) intraperitoneally. After being anesthetized, C57BL/6 female mice (n=3 per group) were randomly divided and prepared for treatment. The animals underwent an acetone-strip three times. The "Revance DYSPORT® solution" was applied to the hind limb using a pipet and massaged into the skin wearing nitrile gloves. Animals recovered in a controlled heat environment to prevent hypothermia. Baseline and post-treatment photographs, video of the animal's recovery and Digital Abduction Score (DAS) values were recorded.

Statistical Analysis:

Statistical analysis was subsequently determined for each group using Statview® software (Abacus Concepts, Berkeley, Calif.) and expressed as mean and standard error. Statistical significance for all comparison was determined using one-factor ANOVA repeated measures and Fisher PLSD post-hoc testing at 95% confidence.

Results:

Foot Mobility Scores were tabulated using DAS values where score of 0 indicates normal digit abduction (no muscle weakening) and a score of 4 indicates maximal reduction in digit abduction (maximal muscle weakening) [Aoki, K. R. A Comparison of the Safety Margins of Botulinum Neurotoxin Serotypes A, B, and F in mice. *Toxicon.* 2001; 39:1815-1820].

Statistical analyses were determined by three different comparisons and the results are presented in Tables 6-8. Mean DAS values showed statistically significant muscle weakening/paralysis between treatment groups versus control after single-time topical administration of "Revance DYSPORT® solution." Table 6 shows the statistically significant paralysis from topical DYSPORT® for each group (P=0.0001) versus control whereas Table 7 details statistically significant paralysis for all treatment groups versus control (P=0.0013). Table 8 details statistically significant paralysis for groups treated with formulation 1 or 2 (P=0.0024) between groups and versus control.

After recovery, animals were observed to walk in circles toward the paralyzed limbs.

TABLE 6

Foot mobility score - DAS values. Mean and standard errors for each group are presented after 30 minutes post treatment.

| Group | Mean | Std. Error |
|---|---|---|
| CL | 2.500 | 0.267 |
| CM | 1.000 | 0.189 |
| CN | 0.375 | 0.183 |
| CO | 0.250 | 0.164 |
| CP | 0.500 | 0.189 |
| Control | 0.333 | 0.333 |

P = 0.0001 (Significant at 95%)

TABLE 7

Foot mobility score - DAS values. Mean and standard errors for all treatment groups versus control are presented.

| Group | Mean | Std. Error |
|---|---|---|
| CL-CP | 0.900 | 0.240 |
| Control | 0.000 | 0.000 |

P = 0.0013 (Significant at 95%)

TABLE 8

Foot mobility score - DAS values. Mean and standard errors for treatment group with formulation 1 or 2 versus control are presented.

| Group | Mean | Std. Error |
|---|---|---|
| CL-CN | 1.400 | 0.400 |
| CO, CP | 0.400 | 0.163 |
| Control | 0.000 | 0.000 |

P = 0.0024 (Significant at 95%)

Conclusion:

This experiment serves to demonstrate that the peptidyl transdermal carrier can transport a therapeutically effective amount of DYSPORT® botulinum therapeutic across skin without covalent modification of the therapeutic.

Example 7

Sweat Inhibition by Topical Botulinum Toxin in a Mouse Hind Foot Model

Purpose:

To determine the sweat inhibition by topical application of botulinum toxin with peptidyl carrier (Revance's botulinum formulation) in a murine model.

Methods:

Study Design:

Female C57BL/6 mice (Charles River, Wilmington, Mass.) weighing 19-21 g were used. Animals were anesthetized using 1.5% isoflurane mixed with oxygen and remained anesthetized for the duration of the study. BOTOX® was applied topically at a dosage of 2 units per mouse foot (Table 9). Sweat was induced by the cholinergic drug pilocarpine. [Kaszynski, E and Frisch S B. Mouse Foot Screen for the Inhibition of Sweating by Anticholinergic Drugs. (1974) Journal of Investigative Dermatology, 62:510-513]. Sweat was visualized with Minor's starch-iodine test.

TABLE 9

Description of test compounds and peptidyl transdermal carrier (backbones)

| Group | Test Compound | Backbone |
|---|---|---|
| BO | 2U BOTOX ® | N/A |
| BP | 2U BOTOX ® | KNR |
| BQ | 2U BOTOX ® | KNT |

Test Compound Preparation:

The pilocarpine solution (Sigma Aldrich, Cat No. P0472) was prepared 24 hours prior to injection. Pilocarpine solution was prepared at 1 milligram/milliliter concentration with 0.9% sodium chloride and mixed well by vortex for 2 minutes. The pilocarpine solution was sterilized by filtration with PURADISC 25 TF disposable filter device (Whatman, 25 mm Dia. Catalog No. 6784-2504) and a large syringe into a sterile vial. Then, the solution was covered with foil. A 2% iodine solution (Sigma Aldrich, Cat No. 266426) in 70% ethanol was prepared and mixed well by vortex. The iodine solution was then sonicated for 15 minutes then vortex again. Backbones were prepared at 1 milligram/milliliter concentration with deionized water. 100 units of BOTOX® (Allergan, Irvine, Calif.) was reconstituted with 1.0 milliliters of 0.9% sodium chloride using sterile 3 ml latex free syringe with $18_G11/2$ (Becton Dickinson & Co., Franklin Lakes, N.J.). The reconstituted BOTOX® was carefully mixed by inversion eight times. Treatment solution was prepared with 7 units of BOTOX® and backbone (i.e. 70 microliters of BOTOX® was added to 35 microliters of KNR or KNT and diluted with 35 microliters of PBS) in a microcentrifuge tube and sat at room temperature for 5 minutes for the complexes to form. Control solution was prepared with BOTOX® and PBS (i.e. 70 microliters of BOTOX® was added to 70 microliters of PBS).

Topical Application:

Animals were anesthetized using 1.5% isoflurane mixed with oxygen and then injected with 0.07 ml rodent anesthetic cocktail (3.75 ml of 100 mg/ml Ketamine, 3.00 ml of 20 mg/ml Xylazine, and 23.25 ml of saline) intraperitoneally and supplemented with isoflurane as necessary. After being anesthetized, C57BL/6 female mice (n=6 per group) were randomized to test groups. Twenty microliters of treatment or control solution were applied to assigned hind feet. The bottoms of the feet were coated completely and liberally with the solution. A pipette tip was used to apply a thin evenly coating of test solution to the feet. Animals recovered in a controlled heat environment to prevent hypothermia. The solutions were dried completely using heat lamp for two minutes, then air dried for five minutes. The hind feet were then coated with approximately 50 microliters of CETAPHIL® cream.

Starch-Iodine Test:

Minors starch iodine test was performed to visualize sweat distribution at baseline and at one week post treatment. Animals were kept fully anesthetized with stable vitals for 10 minutes before the iodine solution was applied by dipping the hind feet into 2% iodine solution. The iodine solution was dried completely using a heat lamp for three minutes, then air dried for five minutes. Starch powder was subsequently applied rubbed in with fingers while wearing powder-free gloves. The excess starch powder was removed with a small paint brush and then the starch power was loosely applied with a compact velour pad to enhance uniformity. Baseline and post-treatment photographs were recorded at 10, 20 and 60 minutes post pilocarpine injection.

Results:

Animal's foot sweat was visualized by Minor's starch-iodine test. Sweat was indicated by blue-black coloration. (Kuttner, C et al. Treatment of Gustatory Sweating with Botulinum toxin A. (2001) Int Poster J Dent Oral Med. 3; 3:poster 82).

The blue-black positive spots were typically best viewed at 50-60 minutes after pilocarpine injection. The starch-iodine test showed that the treatment groups had markedly less blue-black positive spots than the control as depicted in the representative photographs in FIGS. 11A-11D.

Example 8

Evaluating Muscle Force Generation after Topical Application of Revance's Botulinum Formulation Purpose:

To evaluate the effects of neuromuscular blockade after topical application of botulinum toxin type B by muscle contraction force generation in a murine model.

Methods:

Study Design:

Male CD1 mice (Charles River, Wilmington, Mass.) weighing 27-33 g were used. Mice were housed in groups of 5 and allowed ad libitum access to food and water before treatment. Animals were anesthetized using 1.5% isoflurane mixed with oxygen and remained anesthetized for the duration of the study. A dose site of each mouse's hind limb was carefully shaved with an Andis Edjer II cordless rechargeable trimmer (Andis, Sturtevant, Wis.). DYSPORT® was applied topically at a dosage of 25 units per mouse limb. Untreated normals, as well as those treated with base formulations (no toxin) applied topically at an equivalent volume served as controls. Muscle contraction force was measured at 2-3.5 hours post topical treatment.

Test Compound Preparation:

The DYSPORT® reconstituting solution of sterile 0.9% sodium chloride (Abbott Laboratories, North Chicago, Ill.) with 5% EtOH and 5% polyaspartate solution was prepared. Backbones were prepared at 1 milligram/milliliter concentration with 0.9% sodium chloride. 500 units of DYSPORT® (Ipsen) was reconstituted with 2.5 milliliters of reconstituting solution using sterile 3 ml latex free syringe with $18_G11/2$ (Becton Dickinson & Co., Franklin Lakes, N.J.). The reconstituted DYSPORT® was carefully mixed by inversion eight times. The Revance's botulinum formulation was prepared with 25 units of DYSPORT® and backbone (i.e. 125 microliters of DYSPORT® was added to 62.5 microliters of proprietary short peptidyl backbone based on prior experiments above) in a microcentrifuge tube and sat at room temperature for 5 minutes for the complexes to form (n=2 animals survived). Control used saline only as an active (n=4 animals).

Topical Application:

The control or Revance's botulinum formulation was applied to the hind limb using a pipet and massaged into the skin wearing nitrile gloves. DYSPORT® and backbones were stored at 4° C. Animals were incubated in a controlled heat environment to prevent hypothermia. Muscle contraction force was measured at 2-3.5 hours post topical treatment.

Muscle contraction force generation: The limb was immobilized by securing it to a wooden table using K-wires through the femur and the tibia to prevent motion. The gastrocnemius was left in situ. A wire suture was tied around the distal end of the Achilles tendon. The tendon was then transected distal to the suture, and the suture was attached to a force transducer (model FT03, Grass, West Warwick, R.I.), which in turn was connected to a force transducer amplifier (model 13-G4615-50, Gould, Cleveland, Ohio). The sciatic nerve from the DYSPORT® treated side was stimulated directly (SD9 stimulator, Grass, West Warwick, R.I.) with increasing voltage until the maximum isometric single-twitch force was obtained. The frequency of stimulation then was increased until maximum tetanic force was generated. Twitch is generated by stimulation of one motor unit, and tetanus is generated by applying summation of all motor units by supermaximal stimulation. The same procedure was repeated on the control limbs. Responses were recorded with a calibrated recording oscillation (RS 3800, Gould, Cleveland, Ohio) linked to the force transducer. (Ma J, Elsaidi G A, Smith T L, et al. Time course of recovery of juvenile skeletal muscle after botulinum toxin A injection, *Am. J. Phys. Med. Rehabil.* 2004; 83(10):774-780)).

Results

Normal values of muscle force generation in a C57BL/6 mice has a mean single twitch force of 60±15 grams and a mean tetanus force of 240±30 grams in a previous study with injection of botulinum toxin A. In this pilot preclinical study, comparable mean single twitch force of 54±2 grams and mean tetanus force of 241±20 grams were found.

When muscle force generation of topical DYSPORT® with Kn21Pr was evaluated, it showed no response resulting in approximately 100% decrease in single twitch and tetanus response in animal treated with single-time administration of topical Revance's botulinum formulation with Kn21Pr versus the controls on the recordings whereas muscle force generation showed approximately 58% decrease in single twitch and approximately 61% decrease in tetanus in animal treated with single-time administration of topical Revance's botulinum formulation with KnT versus the controls for the lower limit. Tables 10 and 11 show the mean and standard error for the single twitch test and the tetanus test respectively.

TABLE 10

Muscle force generation - Single twitch test. Mean and standard errors for treatment group versus control are presented.

| Animal group | Mean | Std. Error |
| --- | --- | --- |
| treatment | 19 | 10.97 |
| control | 45* | 0.00 |

*lower limit

TABLE 11

Muscle force generation - Tetanus test. Mean and standard errors for treatment group versus control are presented.

| Animal group | Mean | Std. Error |
| --- | --- | --- |
| treatment | 81 | 46.765 |
| control | 210* | 0.00 |

*lower limit

Conclusion:

This study serves to demonstrate that topical application of DYSPORT® at 25 units per mouse limb can effectively decrease motor force generation and shows evidence of therapeutic benefits.

Example 9

Evaluating Muscle Force Generation after Topical Application of Revance's Botulinum Formulation Purpose:

To evaluate the effects of neuromuscular blockade after topical application of botulinum toxin type A by muscle contraction force generation in a murine model.

Methods:

Study Design:

Male CD1 mice (Charles River, Wilmington, Mass.) weighing 27-33 g were used. Mice were housed in groups of 5 and allowed ad libitum access to food and water before treatment. Animals were anesthetized using 1.5% isoflurane mixed with oxygen and remained anesthetized for the duration of the study. A dose site of each mouse's hind limb was carefully shaved with an Andis Edjer II cordless rechargeable trimmer (Andis, Sturtevant, Wis.). BOTOX® was applied topically at a dosage of 10 units per mouse limb. Untreated normals, as well as those treated with base formulations (no toxin) applied topically at an equivalent volume served as controls. Muscle contraction force was measured at 2-3.5 hours post topical treatment.

Test Compound Preparation:

The BOTOX® reconstituting solution of sterile 0.9% sodium chloride (Abbott Laboratories, North Chicago, Ill.) with 5% EtOH and 5% polyaspartate solution was prepared. Backbones were prepared at 1 milligram/milliliter concentration with 0.9% sodium chloride. 100 units of BOTOX® (Allergan, Irvine, Calif.) was reconstituted with 1.0 milliliters of reconstituting solution using sterile 3 ml latex free syringe with $18_G11/2$ (Becton Dickinson & Co., Franklin Lakes, N.J.). The reconstituted BOTOX® was carefully mixed by inversion eight times. The "Revance BOTOX® solution" was prepared with 10 units of BOTOX® and backbone (i.e. 100 microliters of BOTOX® was added to 50 microliters of proprietary short peptidyl backbone based on prior experiments above) in a microcentrifuge tube and sat at room temperature for 5 minutes for the complexes to form (n=2 animals survived). Control used saline only as an active (n=4 animals).

Procedures:

The control or "Revance BOTOX® solution" was applied to the hind limb using a pipet and massaged into the skin wearing nitrile gloves. BOTOX® and backbones were stored at 4° C. Animals were incubated in a controlled heat environment to prevent hypothermia. Muscle contraction force was measured at 2-3.5 hours post topical treatment.

Muscle Contraction Force Generation:

The limb was immobilized by securing it to a wooden table using K-wires through the femur and the tibia to prevent motion. The gastrocnemius was left in situ. A wire suture was tied around the distal end of the Achilles tendon. The tendon was then transected distal to the suture, and the suture was attached to a force transducer (model FT03, Grass, West Warwick, R.I.), which in turn was connected to a force transducer amplifier (model 13-G4615-50, Gould, Cleveland, Ohio). The sciatic nerve from the BOTOX® treated side was stimulated directly (SD9 stimulator, Grass, West Warwick, R.I.) with increasing voltage until the maximum isometric single-twitch force was obtained. The frequency of stimulation then was increased until maximum tetanic force was generated. Twitch is generated by stimulation of one motor unit, and tetanus is generated by applying summation of all motor units by supermaximal stimulation. The same procedure was repeated on the control limbs. Responses were recorded with a calibrated recording oscillation (RS 3800, Gould, Cleveland, Ohio) linked to the force transducer. [Ma J, Elsaidi G A, Smith T L, et al. Time course of recovery of juvenile skeletal muscle after botulinum toxin A injection. *Am. J. Phys. Med. Rehabil.* 2004; 83(10):774-780].

Results:

Normal values of muscle force generation in a C57BL/6 mice as performed here are mean single twitch force of 60±15 grams and mean tetanus force of 240±30 grams. In this pilot preclinical study, comparable mean single twitch force of 54±2 grams and mean tetanus force of 241±20 grams were found.

Figure 10A:
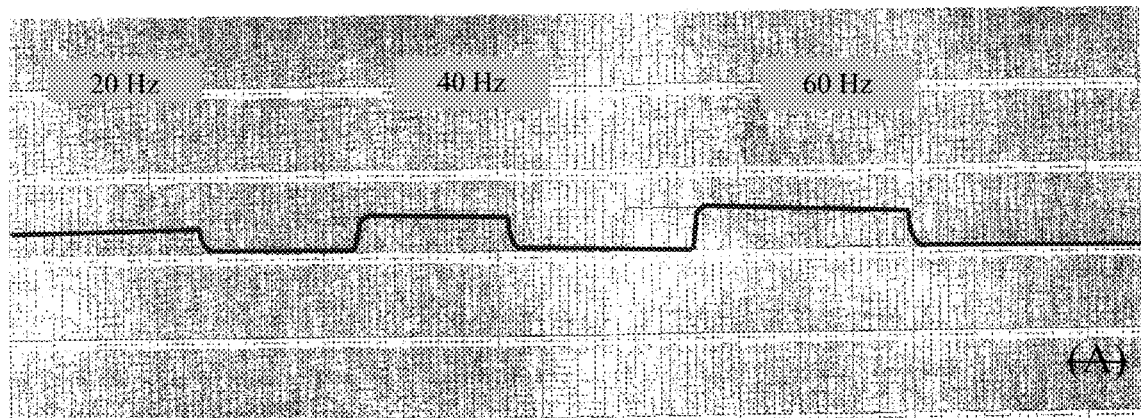
FIGS. 10A and 10B.
Figure 10B:
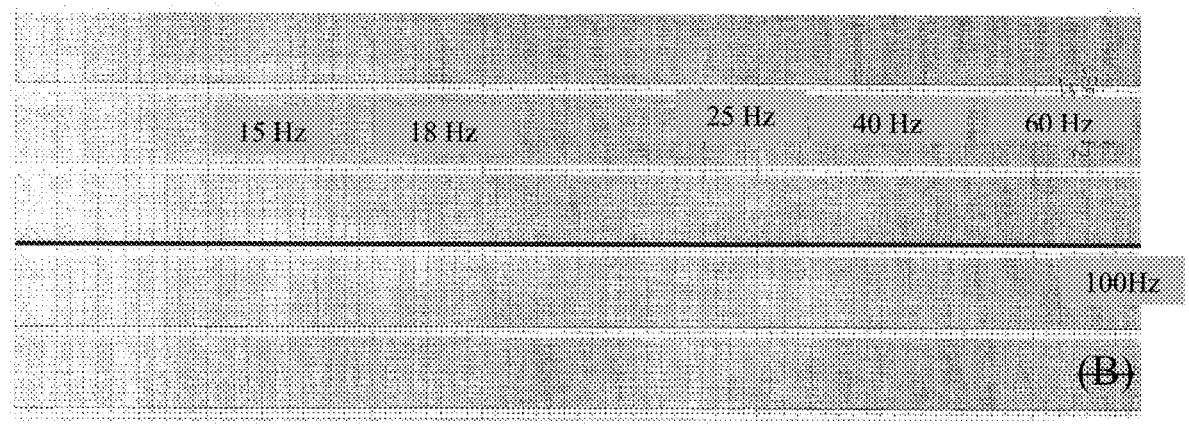
Figure 11A:
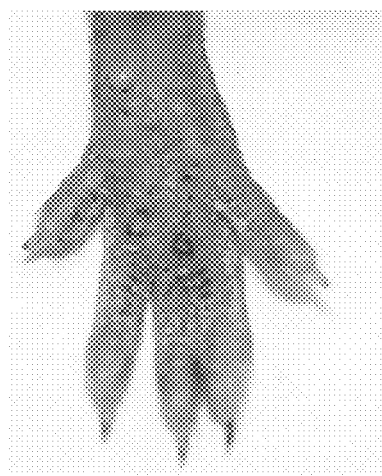
FIGS. 11A-11D show mouse foot sweat production visualized by iodine-starch staining (blue-black positives) 7 days after topical application of botulinum toxin without carrier (Figures A and C) or botulinum toxin with KNR (Figures B and D) in two different animals as described in Example 7.
Figure 11B:
Figure 11C:
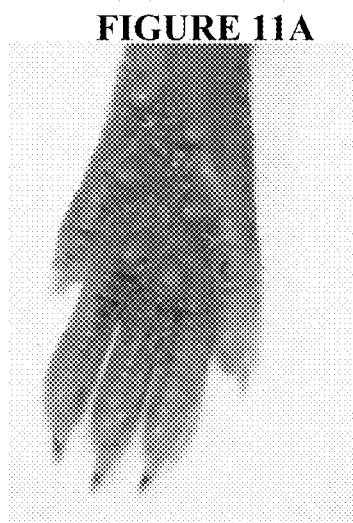
Figure 11D:

When muscle force generation of topical BOTOX® with Kn21Pr was evaluated, it showed no response resulting in approximately 100% decrease in single twitch and tetanus response in animal treated with single-time administration of topical "Revance BOTOX® solution" with Kn21Pr versus the controls on the recordings (FIGS. 10A and 10B) whereas muscle force generation showed approximately 90% decrease in single twitch and 100% decrease (no response) in tetanus in animal treated with single-time administration of topical "Revance BOTOX® solution" with KNP versus the controls. Table 12 shows the mean and standard error for the single twitch test and the tetanus test respectively. Table 13 shows the summary of mean muscle force generation and percentage of decrease for single twitch and tetanus.

TABLE 12

Muscle force generation - Tetanus test. Mean and standard errors for treatment group versus control are presented.

| Animal group | Mean | Std. Error |
| --- | --- | --- |
| treatment | 4.667 | 4.667 |
| control | 45 | 0 |

*lower limit

TABLE 13

Summary of muscle force generation studies from Examples 8 and 9. Mean values and % of decrease for treatment group versus control are presented.

| Treatment | Carrier | Muscle Force Generation | Mean Results (g) | Mean % decrease |
| --- | --- | --- | --- | --- |
| BOTOX® | Kn21T(2)/ Kn21pr(1) | single twitch tetanus | 5 0 | 90% 100% |
| DYSPORT® | Kn21T/Kn21pr | single twitch tetanus | 19 81 | 58% 61% |
| Control | N/A | single twitch tetanus | 45* 210* | 0% 0% |

*lower limit

Conclusion:

This study serves to demonstrate that topical application of both DYSPORT® at 25 units per mouse limb and BOTOX® at 10 units per mouse limb can effectively decrease motor force generation and shows evidence of therapeutic benefits.

Example 10

In Vitro Carrier-Mediated Transdermal Delivery of Botulinum Toxin Type A Across Porcine Skin—Pt. 1 Flow-Through Analysis Purpose:

To evaluate the efficiency of our carrier in delivering Botulinum Toxin Type A (BoNTA) across the skin barrier.

Methods:

Biotinylating Toxin:

10 micrograms of Botulinum Toxin Type A (List Biological Laboratories, Campbell, Calif.) was resuspended in 100 microliters of PBS, pH 7.4. Sulfo-NHS-LC-Biotin (Pierce, Rockford, Ill.) was added at a 20-fold molar excess, and the reaction volume was brought to 1 milliliter. Reaction was incubated at room temperature for 1 hour, and dialyzed against PBS overnight using a 10 K MWCO Slide-A-Lyzer Dialysis Cassette (Pierce, Campbell, Calif.).

Harvesting Skin:

Intact skin was harvested from male and female pig abdomen (Lychron LLC, Mountain View, Calif.). During transport, skin was immersed in an ice bath containing PBS, 10 unit/milliliters Penicillin, and 10 micrograms/milliliters Streptomycin. Epidermis and dermis were isolated using a Dermatome (Padgett Instruments, Plainsboro, N.J.) set at a thickness of 0.8 mm. Skin was snap-frozen in liquid nitrogen and stored at −80° C. until use.

Testing:

All experimental conditions were tested in triplicate. For each sample, appropriate amounts of carrier and toxin were added (Table 14) and the volume was brought to 200 microliters with PBS.

TABLE 14

Description of test sample composition

| Toxin (μg) | 0.05 | 0.05 | 0.05 | 0.1 | 0.1 | 0.1 | 1 | 1 | 1 |
|---|---|---|---|---|---|---|---|---|---|
| Carrier | K30T | K30T | K30T | K30T | K30T | K30T | K30T | K30 | None |
| Carrier (μg) | 0.025 | 0.05 | 0.1 | 0.05 | 0.1 | 0.2 | 1 | 1 | — |

Figures 12A, 12B:
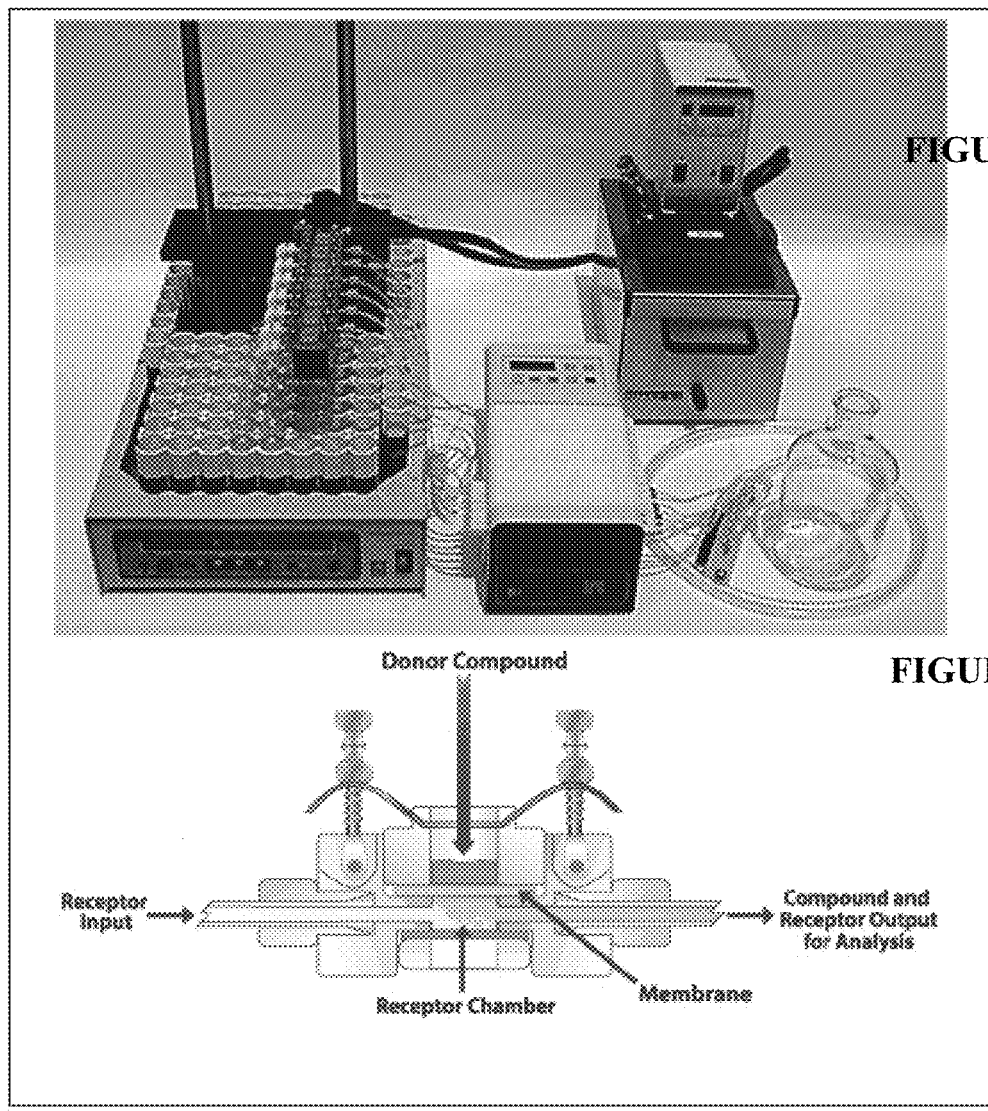
FIGS. 12A and 12B: Modified Franz Chamber.

Skin was thawed in a 37° C. water bath immediately before use, sectioned into 1.5 cm×1.5 cm squares, and secured inside the modified Franz Chamber apparatus (PermeGear, Bethlehem, Pa.). A Haake DC10 circulating water bath (Thermo Electron, Karlsruhe, Germany) was set at 37° C. Samples were applied to the skin surface, and the flow-through rate was set at 8.02 microliters/minute using an IPC Ismatec peristaltic pump (Idex, Wertheim-Mondfeld, Germany). Flow-through fractions were collected using a Retriever IV fraction collector (Teledyne Isco, Lincoln, Nebr.) pooled at hours 0-1, 1-2, 2-3, 3-4, 4-6, 6-8, 8-12, and 12-20 using an ATM10 Indexing Controller (Permegear, Bethlehem, Pa.). See FIGS. 12A-12B for apparatus setup.

Sample Analysis: Serial dilutions of biotinylated toxin solution were performed for standard curve. A plate was coated with 200 microliters flow-through samples and standards and incubated at room temperature for 2 hours. The plate was then washed 3 times with 0.1% TWEEN 20 in PBS (PBST). 200 microliters of blocking buffer/well (20% FBS in PBST) was then added and incubated at room temperature for 2 hours. Blocking buffer was removed. 100 microliters of Streptavidin-HRP at 1:1000 in 2% FBS in PBST was added to each well, and was incubated at room temperature for 1 hour. The plate was then washed 5 times with PBST. 100 microliters OptEIA substrate (BD Biosciences) was added to each well and incubated at room temperature for 10 minutes to develop. 50 microliters 1N $H_2SO_4$ was added to quench the reaction, and absorption was measured at 450 nm.

Results:

Revance carrier showed an increase in toxin delivery (see FIGS. 13A-13B). Optimizing the toxin concentration and carrier:toxin mass ratio yielded a statistically significant (P<0.05) increase in toxin delivery versus controls.

Example 11

In Vitro Carrier-Mediated Transdermal Delivery of Botulinum Toxin Type A Across Porcine Skin—Pt. 2 Flow-Through Analysis Purpose:

To evaluate the efficiency of Revance carriers in delivering Botulinum Toxin Type A and Calf Intestinal Phosphatase (CIP) across the skin barrier in a porcine skin model using modified Franz chambers.

Methods:

Biotinylating Toxin:

10 micrograms of Botulinum Toxin Type A (List Biological Laboratories, Campbell, Calif. and Sigma-Aldrich) was resuspended in 100 microliters of PBS, pH 7.4. Sulfo-NHS-LC-Biotin (Pierce, Rockford, Ill.) was added at a 20-fold molar excess, and the reaction volume was brought to 1 milliliter with PBS. The pH was check to ensure a pH range of 7-9 for coupling. Reaction was incubated at room temperature for 1 hour, and dialyzed against PBS overnight using a 10 K MWCO Slide-A-Lyzer Dialysis Casette (Pierce, Campbell, Calif.).

Harvesting Skin:

Intact skin was harvested from male and female pig abdomens and shoulders (Lychron LLC, Mountain View, Calif.). During transport, skin was immersed in an ice bath containing PBS, 10 unit/milliliters Penicillin, and 10 micrograms/milliliters Streptomycin. Skin grafts (full thickness including epidermis and dermis) were isolated using a Dermatome (Padgett Instruments, Plainsboro, N.J.) set at a thickness of 0.8 mm. Skin grafts were snap-frozen in liquid nitrogen and stored at −80° C. until use.

Testing:

Experimental conditions were tested in triplicate. There were three payload groups and six different carriers. For each sample, appropriate amounts of carrier and toxin were added (Table 15). The payload and carriers were prepared in following concentrations: Kn8 carriers (Kn8, Kn8R and Kn8T) were prepared at 10 milligrams/milliliter; Kn21T carrier was prepared at 1 milligram/milliliter; K30T and Kn21pR and Botulinum Toxin Type A (List Labs and Sigma toxins) were prepared at 0.1 milligram/milliliter; CIP was prepared at 100 units/milliliter.

TABLE 15

Description of test sample composition

| Sample | Payload | Payload amount (μL) | Carrier | Carrier amount (μL) | PBS (μL) |
|---|---|---|---|---|---|
| 1 | CIP | 100 | Kn8 | 100 | 0 |
| 2 | CIP | 100 | Kn8R | 100 | 0 |
| 3 | CIP | 100 | Kn8T | 100 | 0 |
| 4 | CIP | 100 | Kn21T | 2.86 | 97.14 |
| 5 | List pure neurotoxin | 100 | K30T | 10 | 90 |
| 6 | List pure neurotoxin | 100 | Kn21pR | 10 | 90 |
| 7 | Sigma neurotoxin + lactose | 100 | K30T | 10 | 90 |
| 8 | Sigma neurotoxin + lactose | 100 | Kn21pR | 10 | 90 |

Skin was thawed in a 37° C. water bath immediately before use, sectioned into 1.5 cm×1.5 cm squares, and secured inside the modified Franz Chamber apparatus (PermeGear, Bethlehem, Pa.). A Haake DC10 circulating water bath (Thermo Electron, Karlsruhe, Germany) was set at 37° C. Samples were applied to the skin surface, and the flow-through rate was set at 8.02 microliters/minute using an IPC Ismatec peristaltic pump (Idex, Wertheim-Mondfeld, Germany). Flow-through fractions were collected using a Retriever IV fraction collector (Teledyne Isco, Lincoln, Nebr.) pooled at hours 0-1, 1-2, 2-3, 3-4, 4-6, 6-8, 8-12, and 12-20 using an ATM10 Indexing Controller (Permegear, Bethlehem, Pa.).

Sample Analysis:

Performed serial dilutions of biotinylated toxin solution were done for standard curve. Plate was coated with 200 microliters flow-through samples and standards and incubated at room temperature for 2 hours. Plate was then washed 3 times with 0.1% TWEEN 20 in PBS (PBST). 200 microliters of blocking buffer/well (20% FBS in PBST) was then added and incubated at room temperature for 2 hours. Blocking buffer was removed. 100 microliters of Streptavidin-HRP at 1:1000 in 2% FBS in PBST was added to each well, and was incubated at room temperature for 1 hour. The plate was then washed 5 times with PBST. 100 microliters OptEIA substrate (BD Biosciences) was added to each well and incubated at room temperature for 10 minutes to develop. 50 microliters 1N $H_2SO_4$ was added to quench the reaction, and absorption was measured at 450 nm.

CIP:

Similar procedure as used for the CIP. CIP was chosen as an alternative because is very similar to botulinum toxin. It is a globular protein with similar molecular weight of 160 kD. It is less expensive and CIP has high specific activity.

Results:

TABLE 16

Summary of efficiency. Mean efficiency and standard errors are shown in percentages.

| Payload | Carrier | Efficiency (%) | Std. Error (%) |
|---|---|---|---|
| CIP | Kn8 | 0.19 | n/a |
| CIP | Kn8R | 0.26 | n/a |
| CIP | Kn8T | 0.34 | n/a |
| CIP | Kn21T | 0.66 | 0.18 |
| List pure neurotoxin | K30T | 9.17 | 1.36 |
| List pure neurotoxin | Kn21pR | 3.56 | 0.41 |
| Sigma neurotoxin + lactose | K30T | 5.44 | 0.19 |
| Sigma neurotoxin + lactose | Kn21pR | 4.61 | 0.59 |

As shown in Table 16, different carriers impact depth and tropism for different complexes. Shorter backbones (Kn8 series) stay more superficial so flow through less readily. TAT penetrates deeper than oligoarginine for a given backbone length. Less charged species like CIP do not form as effective particles so do not penetrate as deeply Complex components such as lactose can shift carrier preferences (or require strategies to form stable particles).

Example 12

In Vitro Carrier-Mediated Transdermal Delivery of Botulinum Toxin Type A Across Porcine Skin—Pt. 3 Flow-Through Analysis Purpose:

To evaluate the efficiency of Revance carrier in delivering Botulinum Toxin Type A across the skin barrier in a porcine skin model using modified Franz chambers.

Methods:

Harvesting Skin:

Intact skin was harvested from female pig shoulder and abdomen (Lychron LLC, Mountain View, Calif.). During transport, skin was immersed in PBS, containing 10 unit/ml Penicillin, and 10 mg/ml Streptomycin and kept it on ice. Skin grafts (full thickness including epidermis and dermis) were isolated using a Dermatome (Padgett Instruments, Plainsboro, N.J.) set at a thickness of 0.8 mm and were snap-frozen in liquid nitrogen and stored at −80° C. until use.

Biotinylating Toxin:

10 µg of Botulinum Toxin Type A (List Biological Laboratories, Campbell, Calif.) was resuspended in 100 µl of PBS, pH 7.4. Sulfo-NHS-LC-Biotin (Pierce, Rockford, Ill.) was added at a 100-fold molar excess, and the reaction volume was brought to 1 ml with PBS. The pH was check to ensure a pH range of 7-9 for coupling. Reaction was incubated at room temperature for 2 hours and dialyzed against PBS overnight using a 10 K MWCO Slide-A-Lyzer Dialysis Casette (Pierce, Campbell, Calif.). Next day, biotinylated toxin is aliquoted (100 µl/tube) and stored at 4° C.

Preparation of Skin for Franz Chamber:

Skin was thawed in a 37° C. water bath immediately before use, sectioned into 1.5 cm×1.5 cm squares, and secured inside the modified Franz Chamber apparatus (PermeGear, Bethlehem, Pa.). A Haake DC10 circulating water bath (Thermo Electron, Karlsruhe, Germany) was set at 37° C. Samples were applied to the skin surface, and the flow-through rate was set at 8.02 µl/minute using an IPC Ismatec peristaltic pump (Idex, Wertheim-Mondfeld, Germany). Flow-through fractions were collected using a Retriever IV fraction collector (Teledyne Isco, Lincoln, Nebr.) pooled at hours 0-1, 1-2, 2-3, 3-4 using an ATM10 Indexing Controller (Permegear, Bethlehem, Pa.).

Formulations:

For each sample, appropriate amounts of carrier and toxin were added. All experimental conditions were tested in quadruplicates. The treatment group was biotinylated toxin with Revance carriers and the control group was biotinylated toxin only. Carrier and Botulinum Toxin Type A were prepared in different mass ratio in order to optimize toxin concentration and toxin:carrier mass ratios.

ELISA (Protein Quantification Assay):

Serial dilutions (1:3 and 1:2) of biotinylated toxin were done for standard curve. Plate was coated with 200 µl flow-through samples and standards and incubated at room temperature for 2 hours. After 2 hours, samples and standards were discarded, the plate was blocked with 300 µl of superblock blocking buffer to each well for 1 minute at room temperature and repeated two times. Blocking buffer was removed and 100 µl of Streptavidin-HRP at 1:1000 in PBST with 2% FBS was added to each well, and was incubated at room temperature for 1 hour. The plate was then washed with 300 µl (per well) PBST (PBS with 0.1% TWEEN-20) for 5 minutes at room temperature and repeated 2 times. After washing, 100 µl of OptEIA substrate (BD Biosciences) was added to each well and incubated at room temperature for 10 minutes to develop. Then 50 µl 1N $H_2SO_4$ was added to quench the reaction, and absorption was measured at 450 nm.

Results:

Revance carrier showed an increase in toxin delivery compared to the controls (see FIGS. 14A-14F).

Example 13

In Vitro Carrier-Mediated Transdermal Delivery of Botulinum Toxin Type a Across Porcine Skin—Skin Analysis Purpose:

To evaluate the efficiency of Revance carrier in delivering Botulinum Toxin Type A across the skin barrier in a porcine skin model using modified Franz chambers.

Methods:

Biotinylating Toxin:

10 micrograms of Botulinum Toxin Type A (List Biological Laboratories, Campbell, Calif.) was resuspended in 100 microliters of PBS, pH 7.4. Sulfo-NHS-LC-Biotin (Pierce, Rockford, Ill.) was added at a 20-fold molar excess, and the reaction volume was brought to 1 milliliter with PBS. The pH was check to ensure a pH range of 7-9 for coupling. Reaction was incubated at room temperature for 1 hour, and dialyzed against PBS overnight using a 10 K MWCO Slide-A-Lyzer Dialysis Casette (Pierce, Campbell, Calif.).

Harvesting Skin:

Intact skin was harvested from female pig shoulder (Lychron LLC, Mountain View, Calif.). During transport, skin was immersed in an ice bath containing PBS, 10 unit/ milliliters Penicillin, and 10 micrograms/milliliters Streptomycin. Skin grafts (full thickness including epidermis and dermis) were isolated using a Dermatome (Padgett Instruments, Plainsboro, N.J.) set at a thickness of 0.8 mm. Skin grafts were snap-frozen in liquid nitrogen and stored at −80° C. until use.

Testing:

All experimental conditions were tested in triplicate. There were two test groups. The treatment group was biotinylated toxin with Revance K30 Ts carrier and the control group was biotinylated toxin only. For each sample, appropriate amounts of carrier and toxin were added (Table 17). Carrier and Botulinum Toxin Type A were prepared at 0.1 milligram/milliliter concentration.

TABLE 17

Description of test sample composition

| Sample | Payload | Payload amount (μL) | Carrier | Carrier amount (μL) | PBS (μL) |
|---|---|---|---|---|---|
| 1 | List toxin | 100 | K30Ts | 10 | 90 |
| 2 | List toxin | 100 | K30Ts | 10 | 90 |
| 3 | List toxin | 100 | K30Ts | 10 | 90 |
| 4 | List toxin | 100 | n/a | N/A | 90 |
| 5 | List toxin | 100 | n/a | N/A | 90 |
| 6 | List toxin | 100 | n/a | N/A | 90 |

Skin was thawed in a 37° C. water bath immediately before use, sectioned into 1.5 cm×1.5 cm squares, and secured inside the modified Franz Chamber apparatus (PermeGear, Bethlehem, Pa.). A Haake DC10 circulating water bath (Thermo Electron, Karlsruhe, Germany) was set at 37° C. Samples were applied to the skin surface, and the flow-through rate was set at 8.02 microliters/minute using an IPC Ismatec peristaltic pump (Idex, Wertheim-Mondfeld, Germany). Flow-through fractions were collected using a Retriever IV fraction collector (Teledyne Isco, Lincoln, Nebr.) pooled at hours 0-1, 1-2, 2-3, 3-4, 4-6, 6-8, 8-12, and 12-20 using an ATM10 Indexing Controller (Permegear, Bethlehem, Pa.).

Streptavidin Staining:

The snap frozen skin was sectioned and hydrated with 0.1% TWEEN 20 in PBS (PBST). The sections were blocked with Blotto blocking buffer for 2 hours at room temperature and then rinsed with PBST for 5 minutes intervals three times. Streptavidin-HRP at 1:1000 in 2% FBS in PBST was added and the sections were incubated at room temperature for 30 minutes and then rinsed with PBST for 5 minutes intervals three times. OptEIA substrate (BD Biosciences) was added and the sections were incubated at room temperature for 3 minutes to develop. The sections were washed with PBST and covered with a coverslip.

Results:

Photographs: Stained sections were photographed with a Retina 1300B camera (Imaging, Burnaby, BC, Canada) on a Nikon E600 microscope with 4× magnification planapochromat objective lenses (FIGS. 15A-15F).

Example 14

Effectiveness of Botulinum Toxin Type a in Causing Muscle Paralysis

Objective:

To study the effectiveness of botulinum toxin type A in causing muscle paralysis in mice after topical application of toxin in Revance's botulinum formulation by muscle force generation test.

Materials and Methods:

Botulinum toxin: Neuronox (Medy-Tox, Inc., Korea) Lot# NNX0502, 100 U/vial; 0.9% NaCl (no preservatives, Abbott Laboratories, North Chicago, Ill.)

Polylysine peptide (carrier): K15T2

Test Groups—10 U Toxin/Mouse, n=4

|  | K15T2 carrier | No carrier |
|---|---|---|
| Neuronox (NNX) | x | x |

Polylysine Peptide/Toxin Complexes Preparation:

Target carrier: albumin/toxin mass ratio=1.1:1

Neuronox Preparation: (0.5 mg Albumin/100 U Toxin)

A 1.1 mg/ml stock solution of K15T2 carrier with 0.9% NaCl in a microcentrifuge tube was made and mixed by vortex. 100 U (1 vial) of NNX was reconstituted with 0.5 ml of 0.9% NaCl by slowly injecting 0.9% NaCl into the side wall of a vial and mixed by gentle inversion. (The concentration was 100 U toxin/0.5 ml). 0.5 ml carrier stock solution was slowly injected from 0.5 ml reconstituted toxin and gently inverted the carrier/toxin vial 10 times, sat at room temperature for 5 minutes with the vial standing upright and then gently inverted again before dosing. (The concentration was 100 U toxin/1.0 ml). 100 μl of the mixture was taken out with 1 ml syringe and a needle. The needle was removed before application. (Final concentration is 10 U toxin/100 μl).

Study Design:

Male CD1 mice (Charles River, Wilmington, Mass.) weighing 22-26 g were used for treatment and 28-31 g for control. Mice were housed in groups of 5 and allowed ad libitum access to food and water before treatment. Animals were anesthetized using 1.5% isoflurane mixed with oxygen and remained anesthetized for the duration of the treatment with a dwell time of 30 minutes. A dose site of each mouse's hind limb was carefully shaved with an Andis Edjer II cordless rechargeable trimmer (Andis, Sturtevant, Wis.). NNX was applied topically at a dosage of 10 units per mouse limb. Toxin without peptidyl carrier applied topically at an equivalent volume served as controls. Muscle contraction force was measured at day 4 post topical treatment.

Topical Application:

Animals were anesthetized with isoflurane mixed with oxygen. 100 μl (10 units) of the carrier/toxin mixture was slowly applied by using 1 ml syringe without a needle to spread to a randomly selected hind leg of the mouse (shaved). The other leg is treated with the control mixture. The mixture was massaged onto the hind leg while wearing nitrile gloves, incubated for 30 minutes while the mouse was under anesthesia, then the dosing site was rinsed with water and wiped with a paper towel to clean off the residue toxin at dose site. After topical application and cleansing, mice were returned to its cage for housing and recovered from anesthesia in heat controlled environment. Animals were observed on daily basis for behavioral signs of systemic toxicity such as reduced respiratory rate, labored breathing, ptosis and mydriasis or muscle paralysis. Muscle force generation was measured at day 4 post treatment.

Muscle Contraction Force Generation:

The limb was immobilized by securing it to a wooden table using K-wires through the femur and the tibia to prevent motion. The gastrocnemius was left in situ. A wire suture was tied around the distal end of the Achilles tendon. The tendon was then transected distal to the suture, and the suture was attached to a force transducer (model FT03, Grass, West Warwick, R.I.), which in turn was connected to a force transducer amplifier (model 13-G4615-50, Gould, Cleveland, Ohio). The sciatic nerve from the NNX treated side was stimulated directly (SD9 stimulator, Grass, West Warwick, R.I.). The frequency of stimulation was increased until maximum tetanic force was generated. Tetanus is generated by applying summation of all motor units by supermaximal stimulation. The same procedure was repeated on the control limbs. Responses were recorded with a calibrated recording oscillation (RS 3800, Gould, Cleveland, Ohio) linked to the force transducer. [Ma J, Elsaidi G A, Smith T L, et al. Time course of recovery of juvenile skeletal muscle after botulinum toxin A injection. *Am. J. Phys. Med. Rehabil.* 2004; 83(10):774-780].

Figure 16:
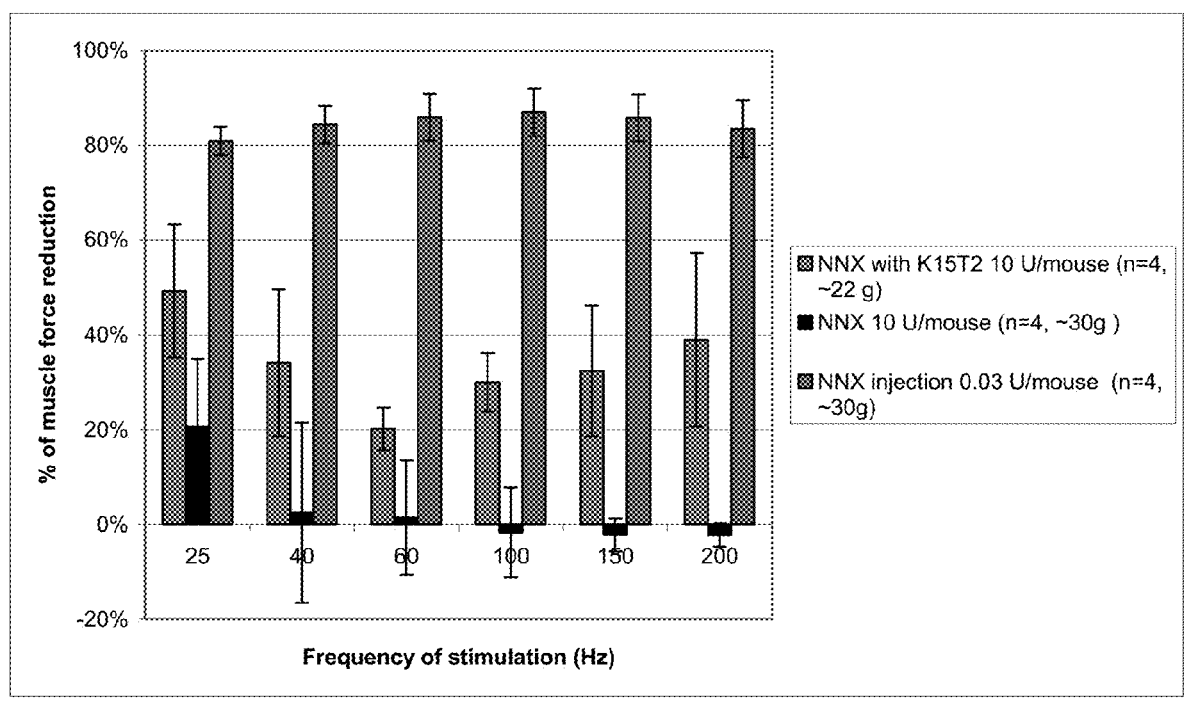
FIG. 16: This figure shows the percentage of muscle for reduction for NNX with K15T2 (treatment group), NNX without carrier (control group), and NNX injection.

Results:

When muscle force generation of topical NNX with peptidyl carrier system was evaluated, it showed reduction in muscle force resulting in approximately 55% decrease in tetanus response in animal treated with single-time topical administration, which had a mean of 128±11 grams for NNX with K15T2 (treatment group) and 286±16 grams for NNX without carrier (control group) (Table 18). Summary of stimulation frequency which includes average percentage of muscle force reduction, mean and standard error for each stimulation frequency are presented in Table 19. FIG. 16 shows the percentage of muscle for reduction for NNX with K15T2 (treatment group), NNX without carrier (control group), and NNX injection.

TABLE 18

Muscle force generation - Tetanus test. Mean and standard errors for treatment group versus control are presented.

| Animal group | Mean | Std. Error |
|---|---|---|
| treatment | 128 | 11 |
| control | 286 | 16 |

Conclusion:

This study demonstrated that botulinum toxin A in Revance's botulinum formulation in proprietary carrier system was effective in causing muscle paralysis in mice after single-time topical application.

Example 15

Human Pilot Study: Topical Botulinum Toxin Type A to Reduce Forehead Wrinkles without Functional Impairment of the Expression Topical Botulinum Toxin Preparation and Application:

Subject 1: First treatment—4 µg of K15T2 Revance Carrier was dissolved in 2.0 ml of 15% poloxamer (in 0.9% sodium chloride and no EtOH) and mixed by inversion. 1.0 ml of poloxamer-Carrier mixture was used to reconstitute 400 U of BOTOX® (Allergan, Irvine, Calif.) in serial steps and mixed by inversion. The final concentration of Carrier to toxin ratio was 0.5 mg Carrier/100 U toxin. The topical toxin solution sat at room temperature for 5 minutes. The total volume of 1.0 ml was applied to forehead using a syringe. After a 30 minute incubation, the treated forehead area was washed with five wet paper towels, where each paper towel was used to wipe the forehead once in one direction only. Photographs were documented at pre-treatment (baseline) and post-treatment.

Subject 2:

First treatment—10 µg of botulinum toxin type A (List Biological Laboratories, Inc., Campbell, Calif., product #130A) was reconstituted in 1.0 ml of 0.9% sodium chloride and the further diluted to a final concentration of 5 ng/100 µl. Reconstituted toxin was mixed by inversion. Revance Carrier was prepared at a concentration 1 ng/20 µl. 1 ng of Carrier was mixed in 900 µl 15% poloxamer in 0.9% NaCl (no EtOH). And then, 100 ml of toxin was added to 920 µl of poloxamer to make a 1:10::toxin:diluent ratio. The total volume of 1.02 ml was applied to forehead using a syringe. After 30 minute incubation, treated forehead area was washed with five wet paper towels in the same manner as subject 1. Photographs were documented at pre-treatment (baseline) and post-treatment.

Results:

FIGS. 17A-17F show photographs taken before and after the treatment. The photographs show reduced forehead

TABLE 19

Summary of stimulation frequency Percentage of muscle force reduction, mean and standard errors are presented.

| Stimulation frequency (Hz) | max force grams | tetanus 25 Hz grams | tetanus 40 Hz grams | tetanus 60 Hz grams | tetanus 100 Hz grams | tetanus 150 Hz grams | tetanus 200 Hz grams |
|---|---|---|---|---|---|---|---|
| NNX + Carrier Group (10U/mouse) % muscle force reduction vs. internal control | | | | | | | |
| std. error | | 14% | 15% | 5% | 6% | 14% | 18% |
| average | | 49% | 34% | 20% | 30% | 32% | 39% |
| Mean | 24 | 30 | 70 | 116 | 128 | 125 | 109 |
| Std. error | 8 | 8 | 16 | 7 | 11 | 25 | 33 |
| NNX Alone - NO Carrier Group (10 U/mouse) % muscle force reduction vs. internal control | | | | | | | |
| std. error | | 14% | 14% | 19% | 12% | 9% | 4% | 2% |
| average | | 3% | 21% | 3% | 1% | -2% | -2% | -2% |
| Mean | | 63 | 76 | 155 | 233 | 284 | 283 | 267 |
| Std. error | | 9 | 14 | 30 | 28 | 16 | 10 | 6 | wrinkles after topical botulinum toxin type A. Human subject 1 (top row) and subject 2 (bottom row) photographs pre-treatment (baseline) and post-treatment.

Example 16

Hyperhidrosis Study—Revance Topical Botulinum Formulation to Treat Excessive Sweating in Human Subjects Purpose:

To determine feasibility of sweat inhibition by topical application of Revance's botulinum formulation.

Preparation:

1 mg/ml of each KNR and P6R-B backbones were prepared in deionized $H_2O$ in separate tubes, vortexed to mix well. BOTOX®—100 units (Allergan, Irvine, Calif.) was reconstituted with either 1.0 ml of deionized $H_2O$ (subject 1) or 0.5 ml of 0.9% NaCl (subject 2 & 3) and mixed by inversion. Stock solution of the treatments was prepared by adding the ingredients shown in the following table to a 1.7 ml microcentrifuge tube, vortexing for 90 seconds, and incubating at room temperature for 5 minutes for allow the complexes to form. The conical tubes were labeled as R for right and L for left. 1.0 ml of stock solution was transferred to assigned conical tubes, 1:5 dilution was prepared by adding 4.0 ml of CETAPHIL® (Galderma, Fort Worth, Tex.) and mixed well using a metal spatula.

| Subject | BOTOX® (U) | Carrier | Ratio (toxin:diluent) | Total volume |
|---|---|---|---|---|
| 1 | 20 | KNR | 5:8 | 1.3 ml |
| 2 | 50 | KNR | 1:1 | 1.5 ml |

Gravimetric Assessment:

Each step of the procedure was performed while wearing nitrile (or powder free) gloves. Three layers of filter paper were prepared and placed in a conical tube using forceps making sure that filter papers were near the screwed top. The filter papers were preweighed in the tubes by placing a tube on its screwed top in the center of the balance pan. Three sets of filter papers were preweighed per subject. The filter papers were placed on each axilla simultaneously. The subjects sat in resting position with their arms by their sides and hands folded in front of the body. Subjects remained still for the collection period in a heated room. After each 10 minute sweat collection period, the filter papers were removed and returned to the their tubes. The filter papers were placed in its original position, unfolded and near the screwed top using forceps using care not to rip the filter papers. Baseline sweat measurements were collected at 10 minutes intervals three times. The filter papers were reweighed by placing a tube on its screwed top in the center of the balance pan and the weight was recorded.

Drug Application Procedure:

While wearing nitrile gloves, 5.0 ml (subject 1) and 1.5 ml (for subject 2) of test article or control was topically applied to axilla using a metal spatula (for subject 1) or rolling applicator (in up and down motion, then circular motion for subject 2). In case of subject 2, each axilla was coated with approximately 4 ml of CETAPHIL® using a small spatula and incubated for 1 hour at room temperature (72-77° F.) to allow the treatment to be absorbed. Axillae were wiped and cleansed with cleansing cloth (Johnson & Johnson).

Observations:

Hair on axillae was intact. Waxing was not done before treatment application. Subjects stated that there was no pain or discomfort. Both sides of axilla had tingling sensation. There were no signs of irritation and no change in skin pigment.

Results

Gravimetric Analysis (Human Subject 1):

Over the first 7 days post topical application of 20 U botulinum toxin (BOTOX®) each axilla with or without the Revance peptidyl carrier for human subject #1 in feasibility trial. Sweat produced (mg) per 10 minutes under standard conditions (p=0.0043)

| | botulinum alone (control) | Revance's botulinum formulation |
|---|---|---|
| % cross-section | 20.5 | 13.4 |

Figure 18:
FIG. 18: Human axillary hyperhidrosis study comparing a formulation according to the invention with a control formulation.

Gravimetric Analysis (Human Subject 2): Over the first 7 days post topical application of 50 U botulinum toxin (BOTOX®) each axilla with or without the Revance peptidyl carrier for human subject #2 in feasibility trial. Sweat produced (mg) per 10 minutes under standard conditions (p=0.0117). FIG. 18 shows a photograph of subject 2 after application of a botulinum toxin formulation according to the invention in one axilla, and the application of a control formulation in the other.

| | Botulinum alone (control) | Revance's Botulinum formulation |
|---|---|---|
| % cross-section | 201 | 157 |

What is claimed is:

1. A method of treating hyperhidrosis in a patient in need thereof, said method comprising:
   topically administering to an affected area of the patient in need of treatment, a pharmaceutically acceptable composition comprising:
   botulinum toxin,
   a carrier comprising a positively charged polymeric backbone with positively charged efficiency groups covalently attached thereto;
   a poloxamer; and
   a dermatologically or pharmaceutically acceptable excipient, diluent, or medium;
   wherein the botulinum toxin is non-covalently associated with the positively charged polymeric backbone; and wherein the carrier comprising the positively charged backbone is the sole necessary agent for non-covalently associating with the botulinum toxin and delivering the botulinum toxin to the affected area so as to treat the hyperhidrosis in said patient.

2. The method according to claim 1, wherein the hyperhidrosis is selected from one or more of axillary hyperhidrosis and forehead hyperhidrosis.

3. The method according to claim 1, wherein the positively charged polymeric backbone is polylysine and the positively charged efficiency groups are amino acid sequences selected from the group consisting of (gly)p-RGRDDRRQRRR-(gly)q (SEQ ID NO: 2), (gly)p-YGRK-KRRQRRR-(gly)q (SEQ ID NO: 3), and (gly)p-RK-KRRQRRR-(gly)q (SEQ ID NO: 4), wherein the subscripts p and q are each independently an integer of from 0 to 20.

4. The method according to claim 1, wherein the positively charged polymeric backbone is polylysine and the positively charged efficiency groups include amino acid sequence (gly)p-RGRDDRRQRRR-(gly)q (SEQ ID NO: 2), wherein the subscripts p and q are each independently an integer of from 2 to 5.

5. The method according to claim 1, wherein the positively charged polymeric backbone is polylysine and the positively charged efficiency groups include amino acid sequence (gly)p-YGRKKRRQRRR-(gly)q (SEQ ID NO: 3), wherein the subscripts p and q are each independently an integer of from 2 to 5.

6. The method according to claim 1, wherein the positively charged polymeric backbone is polylysine and the positively charged efficiency groups include amino acid sequence (gly)p-RKKRRQRRR-(gly)q (SEQ ID NO: 4), wherein the subscripts p and q are each independently an integer of from 2 to 5.

7. The method according to claim 4, wherein the botulinum toxin is of serotype A.

8. The method according to claim 5, wherein the botulinum toxin is of serotype A.

9. The method according to claim 6, wherein the botulinum toxin is of serotype A.

10. The method according to claim 7, wherein the botulinum toxin has a molecular weight of 150,000.

11. The method according to claim 8, wherein the botulinum toxin has a molecular weight of 150,000.

12. The method according to claim 9, wherein the botulinum toxin has a molecular weight of 150,000.

13. The method according to claim 7, wherein the amino acid sequence is attached to the polylysine via either the C-terminus or the N-terminus of the amino acid sequence.

14. The method according to claim 8, wherein the amino acid sequence is attached to the polylysine via either the C-terminus or the N-terminus of the amino acid sequence.

15. The method according to claim 9, wherein the amino acid sequence is attached to the polylysine via either the C-terminus or the N-terminus of the amino acid sequence.

16. The method according to claim 3, wherein the composition comprises botulinum toxin of serotype, and polylysine having covalently attached thereto positively charged efficiency groups having the amino acid sequence (gly)p-RKKRRQRRR-(gly)q (SEQ ID NO. 4), wherein the subscripts p and q are each independently an integer of from 0 to 20.

17. The method according to claim 16, wherein the positively charged efficiency groups comprise from about 0.1% to about 30% by weight of the total carrier weight in the composition.

18. The method according to claim 16, wherein the polylysine has a molecular weight of about 21,000.

19. The method according to claim 16, wherein the botulinum toxin of serotype A has a molecular weight of 150,000.

20. The method according to claim 1, wherein the dermatologically or pharmaceutically acceptable excipient, diluent, or medium is an aqueous diluent comprising a saline solution of 15% poloxamer, and wherein the carrier and the botulinum toxin are present in the saline solution in a ratio corresponding to 0.5 µg carrier to 100 U of toxin.

* * * * *